(12) United States Patent
Sinha

(10) Patent No.: US 11,345,953 B2
(45) Date of Patent: May 31, 2022

(54) DEVELOPMENT OF A HIGHLY SENSITIVE QUANTIFICATION SYSTEM FOR ASSESSING DNA DEGRADATION AND QUALITY IN FORENSIC SAMPLES

(71) Applicant: Life Genetics Lab, LLC, New Orleans, LA (US)

(72) Inventor: Sudhir Sinha, New Orleans, LA (US)

(*) Notice: Subject to any disclaimer, the term of this patent is extended or adjusted under 35 U.S.C. 154(b) by 344 days.

(21) Appl. No.: 15/920,392

(22) Filed: Mar. 13, 2018

(65) Prior Publication Data

US 2018/0230525 A1    Aug. 16, 2018

Related U.S. Application Data

(62) Division of application No. 13/964,970, filed on Aug. 12, 2013, now Pat. No. 9,957,557.

(60) Provisional application No. 61/793,595, filed on Mar. 15, 2013, provisional application No. 61/767,668, filed on Feb. 21, 2013, provisional application No. 61/682,507, filed on Aug. 13, 2012.

(51) Int. Cl.
| | | |
|---|---|---|
| C12P 19/34 | (2006.01) | |
| C12Q 1/6851 | (2018.01) | |
| C12Q 1/6876 | (2018.01) | |

(52) U.S. Cl.
CPC ......... C12Q 1/6851 (2013.01); C12Q 1/6876 (2013.01); *C12Q 2600/16* (2013.01); *C12Q 2600/166* (2013.01)

(58) Field of Classification Search
USPC ......... 435/6.1, 6.11, 6.12, 91.1, 91.2, 91.51; 436/94, 501; 536/23.1, 24.3, 24.33, 25.3, 536/25.32
See application file for complete search history.

(56) References Cited

U.S. PATENT DOCUMENTS

| | | | |
|---|---|---|---|
| 5,210,015 | A | 5/1993 | Gelfand et al. |
| 5,487,972 | A | 1/1996 | Gelfand et al. |
| 5,925,517 | A | 7/1999 | Tyagi et al. |
| 6,103,476 | A | 8/2000 | Tyagi et al. |
| 6,268,130 | B1 | 7/2001 | Kleyn et al. |
| 6,569,627 | B2 | 5/2003 | Wittwer et al. |
| 7,991,558 | B2 | 8/2011 | Kurnik |
| 8,741,573 | B2 | 6/2014 | Sjoblom et al. |
| 2005/0009048 | A1 | 1/2005 | Sagner et al. |
| 2006/0099620 | A1 | 5/2006 | Walker et al. |
| 2006/0199217 | A1 | 9/2006 | Sinha et al. |
| 2006/0289312 | A1 | 12/2006 | Tremblay et al. |
| 2008/0206755 | A1 | 8/2008 | Sinha et al. |
| 2011/0021974 | A1 | 1/2011 | Shantha et al. |
| 2014/0095080 | A1 | 4/2014 | Kurnik |

FOREIGN PATENT DOCUMENTS

| | | |
|---|---|---|
| CN | 102134595 | 7/2011 |
| WO | 2004/081186 | 9/2004 |
| WO | 2007/100530 | 9/2007 |
| WO | 2011/042920 | 4/2011 |
| WO | 2012038503 | 3/2012 |

OTHER PUBLICATIONS

Wehrle et al., Detection of Bacillus cereus with enteropathogenic potential by multiplex real-time PCR based on SYBR green I. Molecular and Cellular Probes, 24, 124-130, 2010.*
Shewale et al., Human Genomic DNA Quantitation System, H-Quant: Development and Validation for Use in Forensic Casework. J. Forensic Sci., 52, 364-370, 2007.*
"TaqMan" from Wikipedia. Printed on Jan. 29, 2021.*
Jothikumar et al., Design of FRET-TaqMan probes for multiplex real-time PCR using an internal positive control. BioTechniques, 46, 519-524, 2009.*
"DNA Polymerase Selection Chart" from New England Biolabs, Inc. Printed on Jan. 29, 2021.*
Almécija et al., Primate Evolution. Fossil apes and human evolution. Science 372, eabb4363, 2021.*
Walker et al., Human DNA quantitation using Alu element-based polymerase chain reaction, Analytical Biochemistry, 315, 122-128, 2003 (Cited in Office action (Paper No. Jul. 2015) dated Jul. 29, 2015 of the parent U.S. Appl. No. 13/964,970, filed Aug. 12, 2013).
Wang et al., SVA Elements: A Hominid-specific Retroposon Family, J. Mol. Biol., 354, 994-1007, 2005 (Cited in Office action (Paper No. Jul. 2015) dated Jul. 29, 2015 of the parent U.S. Appl. No. 13/964,970, filed Aug. 12, 2013).
Hughes et al., Genomics and Genetics of Human and Primate Y Chromosomes, Annu. Rev. Genomics Hum. Genet., 13, 83-108, 2012 (Cited in Office action (Paper No. Jul. 2015) dated Jul. 29, 2015 of the parent U.S. Appl. No. 13/964,970, filed Aug. 12, 2013).

(Continued)

*Primary Examiner* — Frank W Lu
(74) *Attorney, Agent, or Firm* — Stonebridge IP, PLLC

(57) ABSTRACT

A process of quantifying the extent of degradation present in a human DNA sample is described. The process makes use of a real time PCR system to separately quantitate within a sample a first retrotransposon interspersed element and a relatively longer second retrotransposon interspersed element, where the longer element is expected to be disrupted at a faster pace than is the shorter element as the sample degrades. In one embodiment, the process makes use of the appearance of the relatively young (on an evolutionary scale) Alu Yb-lineage subfamily sequences appearing in every human genome and their virtual absence in non-human samples. In a preferred embodiment, the process quantifies longer 290 bp sequences of "SVA" elements and shorter 80 bp sequences of Alu Yb8-lineage. Newly designed primers and TaqMan probes that are useful in the process are presented. A related process additionally quantifies male specific human DNA.

15 Claims, 20 Drawing Sheets
(19 of 20 Drawing Sheet(s) Filed in Color)
Specification includes a Sequence Listing.

(56) References Cited

OTHER PUBLICATIONS

Matuk, Retinitis pigmentosa and retinal degeneration in animals: a review, Can. J. Biochem. Cell Biol., 62(6): 535-546, 1984, abstract (Cited in IDS filed on Oct. 29, 2015 of the parent U.S. Appl. No. 13/964,970, filed Aug. 12, 2013).

Nicklas et al., Development of an Alu-based, real-time PCR method for quantitation of human DNA in forensic samples, J. Forensic. Sci., 48(5): 936-944, 2003 (Cited in Office action (Paper No. Feb. 2016) dated Feb. 11, 2016 of the parent U.S. Appl. No. 13/964,970, filed Aug. 12, 2013).

Nicklas et al., Development of a Real-Time Method to Detect DNA Degradation in Forensic Samples, J. Forensic Sci., 57(2): 466-471, 2012 (Cited in Office action (Paper No. Feb. 2016) dated Feb. 11, 2016 of the parent U.S. Appl. No. 13/964,970, filed Aug. 12, 2013).

Chinese Office Action issued by Chinese Patent Office dated Mar. 21, 2016 in connection with Chinese Patent Application No. 201380052972.9 corresponding to U.S. Appl. No. 13/964,970 and Request for Entry of the Accompanying Office Action attached herewith (Cited in IDS filed on Apr. 26, 2016 of the parent U.S. Appl. No. 13/964,970, filed Aug. 12, 2013).

Swango et al., A quantitative PCR assay for the assessment of DNA degradation in forensic samples, Forensic Science International, 158, pp. 14-26, 2006 (Cited in IDS filed on Apr. 26, 2016 of the parent U.S. Appl. No. 13/964,970, filed Aug. 12, 2013).

Hudlow et al., A quadruplex real-time qPCR assay for the simultaneous assessment of total human DNA, human male DNA, DNA degradation and the presence of PCR inhibitors in forensic samples: A diagnostic tool for STR typing, Forensic Science International: Genetics 2, pp. 108-125, 2008 (Cited in IDS filed on Apr. 26, 2016 of the parent U.S. Appl. No. 13/964,970, filed Aug. 12, 2013).

European Search Report dated Mar. 15, 2016 by the European Patent Office in connection with European Patent Application No. 13829192.7 corresponding to U.S. Appl. No. 13/964,970, (Cited in IDS filed on Apr. 26, 2016 of the parent U.S. Appl. No. 13/964,970, filed Aug. 12, 2013).

Stangegaard et al., Evaluation of Four Automated Protocols for Extraction of DNA from FTA Cards, Journal of Laboratory Automation, 18(5): pp. 404-410, 2013 (Cited in IDS filed on Jun. 9, 2016 of the parent U.S. Appl. No. 13/964,970, filed Aug. 12, 2013).

Lee et al., Allelic discrimination by nick-translation PCR with fluorogenic probes, Nucleic Acids Research, 21(16): 3761-3766, 1993 (Cited in IDS filed on Apr. 11, 2017 of the parent U.S. Appl. No. 13/964,970, filed Aug. 12, 2013).

Tyagi et al., Molecular Beacons: Probes that Fluoresce upon Hybridization, Nature Biotechnology, 14, pp. 303-308, 1996 (Cited in IDS filed on Apr. 11, 2017 of the parent U.S. Appl. No. 13/964,970, filed Aug. 12, 2013).

Butler et al., The Development of Reduced Size STR Amplicons as Tools for Analysis of Degraded DNA, J. Forensic Sci., 48(5): 1054-1064, 2003 (Cited in IDS filed on Apr. 11, 2017 of the parent U.S. Appl. No. 13/964,970, filed Aug. 12, 2013).

Parsons et al., Application of novel "mini-amplicon" STR multiplexes to high volume casework on degraded skeletal remains, Forensic Science International: Genetics 1, 175-179, 2007 (Cited in IDS filed on Apr. 11, 2017 of the parent U.S. Appl. No. 13/964,970, filed Aug. 12, 2013).

Nicklas et al., Development of a Real-Time Method to Detect DNA Degradation in Forensic Samples, J. Forensic Sci., 57(2): 466-471, 2012 (Cited in IDS filed on Apr. 11, 2017 of the parent U.S. Appl. No. 13/964,970, filed Aug. 12, 2013).

Walker et al., Multiplex polymerase chain reaction for simultaneous quantitation of human nuclear, mitochondrial, and male Y-chromosome DNA: application in human identification, Analytical Biochemistry, 337, pp. 89-97, 2005 (Cited in IDS filed on Apr. 11, 2017 of the parent U.S. Appl. No. 13/964,970, filed Aug. 12, 2013).

Carter et al., Genome-wide analysis of the human Alu Yb-lineage, Human Genomics, 1(3): 167-178, 2004 (Cited in IDS filed on Apr. 11, 2017 of the parent U.S. Appl. No. 13/964,970, filed Aug. 12, 2013).

Shen et al., Structure and Genetics of the Partially Duplicated Gene RP Located Immediately Upstream of the Complement C4A and the C4B Genes in the HLA Class III Region, J. Biol. Chem., 269(11): 8466-8476, 1994 (Cited in IDS filed on Apr. 11, 2017 of the parent U.S. Appl. No. 13/964,970, filed Aug. 12, 2013).

Stewart et al., A Comprehensive Map of Mobile Element Insertion Polymorphisms in Humans, PLoS Genetics, 7(8): e1002236, 2011 (Cited in Notice of Allowance (Paper No. Nov. 2017) dated Dec. 13, 2017 of the parent U.S. Appl. No. 13/964,970, filed Aug. 12, 2013).

Development and usage of a NIST standard reference material for real time PCR quantitation of human DNA By: P.M. Vallone, M.C. Kline, D.L. Duewer, A.E. Decker, J.W. Redman, J.C. Travis, M.V. Smith, J.M. Butler. Forensic Sci. Int. Genet. Suppl. Ser. 1 (2008) 80-82.

LINEs and SINEs of Primate Evolution By: M.K. Konkel, J.A. Walker, M.A. Batzer. Evolutionary Anthropology 19:236-249 (2010).

* cited by examiner

Standard Curve

SEQUENCE LISTING

```
<160> NUMBER OF SEQ ID NOS: 27

<210> SEQ ID NO 1
<211> LENGTH: 23
<212> TYPE: DNA
<213> ORGANISM: Artificial
<220> FEATURE:
<223> OTHER INFORMATION: A first forward primer for determining an
      approximately 250 base pair fragment in the alu Ya5 subfamily in a
      human nuclear DNA quantitation assay
```

```
<400> SEQUENCE: 1
tcacgcctgt aatcccagca ctt                                              23

<210> SEQ ID NO 2
<211> LENGTH: 23
<212> TYPE: DNA
<213> ORGANISM: Artificial
<220> FEATURE:
<223> OTHER INFORMATION: A second forward primer for determining an
      approximately 250 base pair fragment in the Alu Ya5 subfamily in a
      human nuclear DNA quantitation assay

<400> SEQUENCE: 2
acgcctgtaa tcccagcact ttg                                              23

<210> SEQ ID NO 3
<211> LENGTH: 20
<212> TYPE: DNA
<213> ORGANISM: Artificial
<220> FEATURE:
<223> OTHER INFORMATION: Reverse primer for determining an approximately
      250 base pair fragment in the Alu Ya5 subfamily in a human nuclear
      DNA quantitation assay

<400> SEQUENCE: 3
tctgtcgccc aggctggagt                                                  20

<210> SEQ ID NO 4
<211> LENGTH: 27
<212> TYPE: DNA
<213> ORGANISM: Artificial
<220> FEATURE:
<223> OTHER INFORMATION: Probe for an approximately 250 base pair
      fragment in the Alu Ya5 subfamily, the probe being useful in a
      human nuclear DNA quantitation assay

<400> SEQUENCE: 4
atcacgaggt caggagatcg agaccat                                          27

<210> SEQ ID NO 5
<211> LENGTH: 20
<212> TYPE: DNA
<213> ORGANISM: Artificial
<220> FEATURE:
<223> OTHER INFORMATION: Forward primer for an approximately 80 base
      pair fragment in the Yb8 Alu subfamily in a human nuclear DNA
      quantitation assay

<400> SEQUENCE: 5
ggaagcggag cttgcagtga                                                  20

<210> SEQ ID NO 6
<211> LENGTH: 22
<212> TYPE: DNA
<213> ORGANISM: Artificial
<220> FEATURE:
<223> OTHER INFORMATION: Reverse primer for an approximately 80 base
      pair fragment in the Yb8 Alu subfamily in a human nuclear DNA
      quantitation assay

<400> SEQUENCE: 6
agacggagtc tcgctctgtc gc                                               22

<210> SEQ ID NO 7
<211> LENGTH: 24
<212> TYPE: DNA
<213> ORGANISM: Artificial
```

-continued

```
<220> FEATURE:
<223> OTHER INFORMATION: Probe for an approximately 80 base pair
      fragment in the Yb8 Alu subfamily in a human nuclear DNA
      quantitation assay

<400> SEQUENCE: 7
agattgcgcc actgcagtcc gcag                                            24

<210> SEQ ID NO 8
<211> LENGTH: 24
<212> TYPE: DNA
<213> ORGANISM: Artificial
<220> FEATURE:
<223> OTHER INFORMATION: Forward primer for an approximately 290 base
      pair SVA fragment useful in a human nuclear DNA quantitation assay

<400> SEQUENCE: 8
tgggatcctg ttgatctgtg acct                                            24

<210> SEQ ID NO 9
<211> LENGTH: 24
<212> TYPE: DNA
<213> ORGANISM: Artificial
<220> FEATURE:
<223> OTHER INFORMATION: Reverse primer for an approximately 290 base
      pair SVA fragment useful in a human nuclear DNA quantitation assay

<400> SEQUENCE: 9
gatttggcag ggtcatggga caat                                            24

<210> SEQ ID NO 10
<211> LENGTH: 26
<212> TYPE: DNA
<213> ORGANISM: Artificial
<220> FEATURE:
<223> OTHER INFORMATION: Probe for an approximately 290 base pair SVA
      fragment useful in a human nuclear DNA quantitation assay

<400> SEQUENCE: 10
aagggcggtg caagatgtgc tttgtt                                          26

<210> SEQ ID NO 11
<211> LENGTH: 24
<212> TYPE: DNA
<213> ORGANISM: Artificial
<220> FEATURE:
<223> OTHER INFORMATION: Forward primer for an SVA fragment useful in a
      human nuclear DNA quantitation assay

<400> SEQUENCE: 11
atgtgctgtg tccactcagg gtta                                            24

<210> SEQ ID NO 12
<211> LENGTH: 24
<212> TYPE: DNA
<213> ORGANISM: Artificial
<220> FEATURE:
<223> OTHER INFORMATION: A first reverse primer for an SVA fragment
      useful in a human nuclear DNA quantitation assay

<400> SEQUENCE: 12
ttcttgggtg tttctcacag aggg                                            24

<210> SEQ ID NO 13
<211> LENGTH: 24
<212> TYPE: DNA
<213> ORGANISM: Artificial
```

```
<220> FEATURE:
<223> OTHER INFORMATION: A second reverse primer for an SVA fragment
      useful in a human nuclear DNA quantitation assay

<400> SEQUENCE: 13
attcttgggt gtttctcaca gagg                                           24

<210> SEQ ID NO 14
<211> LENGTH: 22
<212> TYPE: DNA
<213> ORGANISM: Artificial
<220> FEATURE:
<223> OTHER INFORMATION: Forward primer for an SVA fragment useful in a
      human nuclear DNA quantitation assay

<400> SEQUENCE: 14
ccaaccctgt gctctctgaa ac                                             22

<210> SEQ ID NO 15
<211> LENGTH: 21
<212> TYPE: DNA
<213> ORGANISM: Artificial
<220> FEATURE:
<223> OTHER INFORMATION: Reverse primer for an SVA fragment useful in a
      human nuclear DNA quantitation assay

<400> SEQUENCE: 15
tttggcaggg tcatgggaca a                                              21

<210> SEQ ID NO 16
<211> LENGTH: 24
<212> TYPE: DNA
<213> ORGANISM: Artificial
<220> FEATURE:
<223> OTHER INFORMATION: Forward primer for a 90 base pair internal
      positive control that is useful for determining an extent of
      inhibition in a human nuclear DNA quantitation assay

<400> SEQUENCE: 16
aaagatcctg ccaacaggac agtg                                           24

<210> SEQ ID NO 17
<211> LENGTH: 24
<212> TYPE: DNA
<213> ORGANISM: Artificial
<220> FEATURE:
<223> OTHER INFORMATION: Reverse primer for a 90 base pair internal
      positive control that is useful for determining an extent of
      inhibition in a human nuclear DNA quantitation assay

<400> SEQUENCE: 17
acagacggta tagagaccaa tcag                                           24

<210> SEQ ID NO 18
<211> LENGTH: 21
<212> TYPE: DNA
<213> ORGANISM: Artificial
<220> FEATURE:
<223> OTHER INFORMATION: Forward primer for a 158 base pair internal
      positive control that is useful for determining an extent of
      inhibition in a human nuclear DNA quantitation assay

<400> SEQUENCE: 18
gcataaagat cctgccaaca g                                              21

<210> SEQ ID NO 19
<211> LENGTH: 21
```

```
<212> TYPE: DNA
<213> ORGANISM: Artificial
<220> FEATURE:
<223> OTHER INFORMATION: Reverse primer for a 158 base pair internal
      positive control that is useful for determining an extent of
      inhibition in a human nuclear DNA quantitation assay

<400> SEQUENCE: 19
accaaagtgc tgcagaaata c                                              21

<210> SEQ ID NO 20
<211> LENGTH: 28
<212> TYPE: DNA
<213> ORGANISM: Artificial
<220> FEATURE:
<223> OTHER INFORMATION: Probe for the internal positive control assay,
      the probe being useful in the assay including three targets--a
      "short" Yb8 Alu fragment, a "long" SVA fragment and the internal
      positive control

<400> SEQUENCE: 20
aggcagagat tgcactgcct taaagtgg                                       28

<210> SEQ ID NO 21
<211> LENGTH: 21
<212> TYPE: DNA
<213> ORGANISM: Artificial
<220> FEATURE:
<223> OTHER INFORMATION: Forward primer for an internal positive control
      that is useful for determining an extent of inhibition in a human
      nuclear DNA quantitation assay incorporating an assay for a male
      specific DNA target sequence to detect male DNA in the sample

<400> SEQUENCE: 21
gcataaagat cctgccaaca g                                              21

<210> SEQ ID NO 22
<211> LENGTH: 20
<212> TYPE: DNA
<213> ORGANISM: Artificial
<220> FEATURE:
<223> OTHER INFORMATION: Reverse primer for a 172 base pair internal
      positive control that is useful for determining an extent of
      inhibition in a human nuclear DNA quantitation assay incorporating
      an assay for a male specific DNA target sequence to detect male
      DNA in the sample

<400> SEQUENCE: 22
gcccgaactt ccaacactat                                                20

<210> SEQ ID NO 23
<211> LENGTH: 20
<212> TYPE: DNA
<213> ORGANISM: Artificial
<220> FEATURE:
<223> OTHER INFORMATION: Reverse primer for a 192 base pair internal
      positive control that is useful for determining an extent of
      inhibition in a human nuclear DNA quantitation assay incorporating
      an assay for a male specific DNA target sequence to detect male
      DNA in the sample

<400> SEQUENCE: 23
attgttcctc ctgcctgatt                                                20

<210> SEQ ID NO 24
<211> LENGTH: 24
<212> TYPE: DNA
<213> ORGANISM: Artificial
<220> FEATURE:
```

```
<223> OTHER INFORMATION: Probe for the internal positive control assay,
      the probe being useful in the assay including four targets--a
      "short" Yb8 fragment, a "long" SVA fragment, a male specific DNA
      target sequence to detect male DNA and the internal positive
      control

<400> SEQUENCE: 24
acagtgtcag gcagagattg cact                                          24

<210> SEQ ID NO 25
<211> LENGTH: 24
<212> TYPE: DNA
<213> ORGANISM: Artificial
<220> FEATURE:
<223> OTHER INFORMATION: Forward primer for male specific DNA target
      sequence for detecting male DNA

<400> SEQUENCE: 25
caatgtgcta ggctctagga atac                                          24

<210> SEQ ID NO 26
<211> LENGTH: 22
<212> TYPE: DNA
<213> ORGANISM: Artificial
<220> FEATURE:
<223> OTHER INFORMATION: Reverse primer for the male specific DNA target
      sequence for detecting male DNA

<400> SEQUENCE: 26
aagagtgtca tggctcaaag ag                                            22

<210> SEQ ID NO 27
<211> LENGTH: 27
<212> TYPE: DNA
<213> ORGANISM: Artificial
<220> FEATURE:
<223> OTHER INFORMATION: Probe for the male specific DNA target sequence
      for detecting male DNA

<400> SEQUENCE: 27
agagagtatg acaaacatgg catgggc                                       27
```

DEVELOPMENT OF A HIGHLY SENSITIVE QUANTIFICATION SYSTEM FOR ASSESSING DNA DEGRADATION AND QUALITY IN FORENSIC SAMPLES

CLAIM OF PRIORITY

This application is a division of, incorporates the same herein, and claims all benefits accruing under 35 U.S.C. § 121 from an application for DEVELOPMENT OF A HIGHLY SENSITIVE QUANTIFICATION SYSTEM FOR ASSESSING DNA DEGRADATION AND QUALITY IN FORENSIC SAMPLES, earlier filed in the United States Patent and Trademark Office under 35 U.S.C. § 111(a) on Aug. 12, 2013, and duly assigned Ser. No. 13/964,970, now U.S. Pat. No. 9,957,557 and makes reference to, incorporates the same herein, and claims all benefits accruing under 35 U.S.C. § 119(e) from another application of the same title earlier filed in the United States Patent and Trademark Office as a provisional application under 35 U.S.C. § 111(b) on Aug. 13, 2012, and duly assigned Ser. No. 61/682,507, another application of the same title earlier filed in the United States Patent and Trademark Office as a provisional application under 35 U.S.C. § 111(b) on Feb. 21, 2013, and duly assigned Ser. No. 61/767,668 and another application of the same title earlier filed in the United States Patent and Trademark Office as a provisional application under 35 U.S.C. § 111(b) on Mar. 15, 2013, and duly assigned Ser. No. 61/793,595.

STATEMENT REGARDING FEDERALLY SPONSORED RESEARCH OR DEVELOPMENT

This invention was made with Government support under SBIR grant #1230352 awarded by the National Science Foundation. The Government has certain rights in this invention.

NUCLEOTIDE SEQUENCE LISTING

Pursuant to 37 C.F.R. § 1.821(e), reference is made to the computer readable form of the nucleotide sequence listing deposited in the United States Patent and Trademark Office on 23 Oct. 2013 as a text file residing on a compact disc to become part of the record of an application for DEVELOPMENT OF A HIGHLY SENSITIVE QUANTIFICATION SYSTEM FOR ASSESSING DNA DEGRADATION AND QUALITY IN FORENSIC SAMPLES, earlier filed in the United States Patent and Trademark Office under 35 U.S.C. § 111(a) on Aug. 12, 2013, and duly assigned Ser. No. 13/964,970. Applicant hereby requests use in the present application of the computer readable "Sequence Listing" that is on file in case number 13/964,970, now U.S. Pat. No. 9,957,557.

BACKGROUND OF THE INVENTION

Field of the Invention

A process for determining the extent of environmental degradation of a human DNA sample by using newly identified target elements in a real time polymerase chain reaction system is disclosed.

Description of the Related Art

In the last recent years, real-time polymerase chain reaction (PCR) chemistry has become the standard for reliably quantifying the amount of genomic and amplifiable DNA in a forensic sample. Commonly used systems include the assessment of total human and male DNA. Examples are Quantifiler® from Life Technologies Corporation, Plexor® from Promega Corporation and Quantiplex® from Qiagen. Currently there are several different approaches used for fluorescence-based quantification assays, including SYBR® Green, Plexor®, TaqMan®, AmpliFluor®, Quantifiler® and Quantiplex®.

Interest has recently grown in using real-time PCR methods to evaluate the extent of degradation of a DNA sample. This may be done using two nuclear DNA targets: a short multi-copy sequence and a long multi-copy sequence. Because the long target sequence will degrade more rapidly than will the short target sequence as a sample is compromised, the ratio of the quantity of the short target to the long target will provide an assessment of the extent of degradation in the sample. Studies on the assessment of degraded DNA in a forensic sample have been published using Alu or mini-satellite targets. However, the assays of previous studies either lack in sensitivity or do not exhibit high PCR efficiencies. Forensic samples vary widely in quantity and quality, making the goal of developing and validating a real-time PCR system for the purposes of quantitating the DNA in these samples and determining the extent of their degradation a challenging one.

The recent advances in mini short tandem repeat (STR) analysis systems have now made it possible to analyze highly compromised samples. Investigators have made great strides in the development of STR amplicons that, compared with traditional STR amplicons, are reduced in size and can be used effectively on DNA samples that have been significantly degraded (see, e.g., J. M. Butler, et al., J. Forensic Sci. 48(5): 1054-1064 (2003); T. J. Parsons, et al., Forensic Science International: Genetics 1: 175-179 (2007)).

Alu are Short Interspersed Elements (SINE), approximately 300 bp insertions which are distributed throughout the human genome in large copy number. The evolution of Alu elements in the human genome over time has made Alu elements well suited for the task of distinguishing human DNA from non-human DNA and for doing testing that is desired to be specific to human DNA. A recent study reports an evaluation of the quality assessment of degraded DNA samples using a Ya5-lineage Alu genetic element (J. A. Nicklas, et al., J. Forensic Sci. 57(2): 466-471 (2012)). A multi-copy intra-Alu based approach for quantifying human specific DNA in an evidence sample has been successfully used to obtain DNA quantification with high sensitivity (J. A. Walker, et al., Anal. Biochem. 337: 89-97 (2005)).

The average age of Yb-lineage subfamily elements is estimated as 2.39 million years. It is estimated that the human genome contains over 1800 Alu Yb family elements and, out of those, approximately 50% are from the Yb8 subfamily. The Alu Yb8 system is known for the presence of a large number of fixed insertions. It has been reported that only 20% of the Yb-lineage Alu elements are polymorphic for insertion presence or absence in the human genome (A. B. Carter, et al., Human Genomics 1(3): 1-13 (2004)). Because a large number of these fixed elements are present in every human genome, the individual specific variation possible when using a multi-copy target quantification system is minimized.

In 1994, Shen, et al., identified a new composite retroposon when they studied the structure of the retinitis pigmentosa (RP) gene (Shen, et al., J. Biol. Chem. 269(11): 8466-8476 (1994)). This new retroposon consisted of the SINE-R element together with a stretch of sequence that shares sequence similarity with Alu sequences. Thus, it was named "SVA" after its main components, Short Interspersed Elements (SINE), Variable Number Tandem Repeats (VNTR) and Alu. SVA elements contain the hallmarks of retrotransposons, in that they are flanked by target site duplications (TSDs), terminate in a poly(A) tail and are occasionally truncated and inverted during their integration into the genome.

SUMMARY OF THE INVENTION

One object of the present invention is to provide a method of quantifying the extent of degradation present in a human DNA sample.

Another object of the invention is to provide a method for quantitating the total amount of human DNA as well as the male DNA in a sample.

Another object of the invention is to provide an internal positive control that will offer increased confidence in the results of the DNA degradation determination by providing an additional assessment for the presence of PCR inhibitors in the sample.

Another object of the invention is to provide a convenient means for analysts to choose from among multiple DNA samples the best one for further analytical attention.

Another object of the invention is to provide an improved means for selecting the optimum analytical method to employ on a particular DNA sample, based on the extent of its degradation.

Another object of the invention is to provide a means of assessing the extent of admixture of non-human DNA with the human DNA sample being tested.

Another object of the invention is to provide a means of assessing the extent of admixture of male and female DNA in the sample being tested.

These and other objects may be attained, in one embodiment of the present invention, from a process for quantitating a human DNA in a sample in order to assess the extent of degradation of the DNA therein by providing a sample to be analyzed, using a real time polymerase chain reaction system to separately quantitate within the sample a first retrotransposon interspersed element and a second retrotransposon interspersed element, the first retrotransposon interspersed element being an Alu element and the second retrotransposon interspersed element being an SVA element of the RP gene, and calculating a ratio of an occurrence within the sample of the first retrotransposon interspersed element to an occurrence of the second retrotransposon interspersed element.

In certain embodiments, the quantitation of the first retrotransposon interspersed element and the second retrotransposon interspersed element may be performed simultaneously.

In certain embodiments, the ratio of an occurrence within the sample of the first retrotransposon interspersed element to an occurrence of the second retrotransposon interspersed element may be used to determine an extent of degradation of the DNA in the sample.

In certain embodiments, the second retrotransposon interspersed element may comprise at least three times as many base pairs as are comprised by the first retrotransposon interspersed element.

In certain embodiments, the process of the invention may further comprise the steps of providing a first probe comprising a first moiety capable of fluorescence at a first diagnostic wavelength and a first quencher capable of quenching the first moiety fluorescence, the first probe being targeted to a first retrotransposon interspersed element, providing a second probe comprising a second moiety capable of fluorescence at a second diagnostic wavelength and a second quencher capable of quenching the second moiety fluorescence, the second probe being targeted to a second retrotransposon interspersed element, providing at least one primer that is useful in the real-time polymerase chain reaction system, the system being capable of amplification of a DNA sample, providing a Taq polymerase enzyme capable of catalyzing the formation of a nucleic acid sequence that is complimentary to one present in the sample, the polymerase enzyme being capable both of cleaving the first probe to separate the first fluorescent moiety from the first quencher and of cleaving the second probe to separate the second fluorescent moiety from the second quencher, treating the sample with the first probe and the second probe, amplifying the sample using the at least one primer and the Taq polymerase enzyme by means of the real-time polymerase chain reaction system, the real time polymerase chain reaction system including a plurality of polymerase chain reaction cycles, illuminating the sample during each real time polymerase chain reaction cycle using an excitation source capable of inducing fluorescence in both the first moiety and the second moiety, measuring the fluorescence emitted from the first moiety and the fluorescence emitted from the second moiety for each real time polymerase chain reaction cycle, determining a threshold cycle number for the first retrotransposon interspersed element and the second retrotransposon interspersed element, and comparing the determined threshold cycle numbers with standard curves for each of the first retrotransposon interspersed element and the second retrotransposon interspersed element to determine a concentration for each of the first retrotransposon interspersed element and the second retrotransposon interspersed element within the sample. When the DNA is degraded due to exposure to the environment, the amount of available longer target sequence for amplification will be less than for a shorter target sequence, hence the ratio of quantities of the longer fragment to the shorter fragment in a given DNA sample is diagnostic of the extent of DNA degradation. In the case of DNA which is not degraded or minimally degraded, the ratio of the two target amounts in the sample will be close to one.

In certain embodiments, the process for quantitating human DNA in a sample may further comprise providing at least one primer selected from the group consisting of a forward primer labeled SEQ ID NO: 5 and a reverse primer labeled SEQ ID NO: 6 (primers for the 79 base pair Yb8 Alu fragment) and providing at least one primer selected from the group consisting of a forward primer labeled SEQ ID NO: 8, a forward primer labeled SEQ ID NO: 11, a forward primer labeled SEQ ID NO: 14, a reverse primer labeled SEQ ID NO: 9, a reverse primer labeled SEQ ID NO: 12, a reverse primer labeled SEQ ID NO: 13 and a reverse primer labeled SEQ ID NO: 15 (primers for the 290 base pair SVA fragment):

```
                                          (SEQ ID NO: 5)
        5' GGAAGCGGAGCTTGCAGTGA 3'

(SEQ ID NO: 6)
        5' AGACGGAGTCTCGCTCTGTCGC 3'

(SEQ ID NO: 8)
        5' TGGGATCCTGTTGATCTGTGACCT 3'
```

```
                                      (SEQ ID NO: 9)
5' GATTTGGCAGGGTCATGGGACAAT 3'

(SEQ ID NO: 11)
5' ATGTGCTGTGTCCACTCAGGGTTA 3'

(SEQ ID NO: 12)
5' TTCTTGGGTGTTTCTCACAGAGGG 3'

(SEQ ID NO: 13)
5' ATTCTTGGGTGTTTCTCACAGAGG 3'

(SEQ ID NO: 14)
5' CCAACCCTGTGCTCTCTGAAAC 3'

(SEQ ID NO: 15)
5' TTTGGCAGGGTCATGGGACAA 3'.
```

Alternatively, in another embodiment, the approximately 80 base pair Yb8 Alu fragment may be paired with the approximately 250 base pair Alu Ya5 fragment as target elements in the inventive process. In these embodiments, the process for quantitating human DNA in a sample may further comprise providing at least one primer selected from the group consisting of a forward primer labeled SEQ ID NO: 5 and a reverse primer labeled SEQ ID NO: 6 (primers for the 79 base pair Yb8 Alu fragment) and providing at least one primer selected from the group consisting of a forward primer labeled SEQ ID NO: 1, a forward primer labeled SEQ ID NO: 2 and a reverse primer labeled SEQ ID NO: 3 (primers for the 250 base pair Alu Ya5 fragment):

```
                                      (SEQ ID NO: 5)
5' GGAAGCGGAGCTTGCAGTGA 3'

(SEQ ID NO: 6)
5' AGACGGAGTCTCGCTCTGTCGC 3'

(SEQ ID NO: 1)
5' TCACGCCTGTAATCCCAGCACTT 3'

(SEQ ID NO: 2)
5' ACGCCTGTAATCCCAGCACTTTG 3'

(SEQ ID NO: 3)
5' TCTGTCGCCCAGGCTGGAGT 3'.
```

In certain embodiments, the first probe may have a sequence labeled SEQ ID NO: 7 (for the 79 base pair Yb8 Alu fragment), and the second probe may be selected from the group consisting of a sequence labeled SEQ ID NO: 4 (for the 250 base pair Alu Ya5 fragment) and a sequence labeled SEQ ID NO: 10 (for the 290 base pair SVA fragment):

```
                                      (SEQ ID NO: 4)
5' ATCACGAGGTCAGGAGATCGAGACCAT 3'

(SEQ ID NO: 7)
5' AGATTGCGCCACTGCAGTCCGCAG 3'

(SEQ ID NO: 10)
5' AAGGGCGGTGCAAGATGTGCTTTGTT 3'.
```

In certain embodiments, the real-time polymerase chain reaction system may operate under the following approximate conditions: 95° C. for 10 minutes; 32-40 cycles of: 95° C. for 15 seconds, 61° C. for 70-120 seconds.

In certain embodiments, an internal positive control may be added to the sample to form a sample mixture. A real-time polymerase chain reaction system may then be used to quantitate the internal positive control within the sample mixture, and an expected occurrence within the sample mixture of the internal positive control may be compared with an occurrence within the sample mixture of the internal positive control. The latter comparison may then be used to determine an extent to which the process was affected by the presence of an inhibitor in the sample.

In certain embodiments, the quantitation of the first retrotransposon interspersed element, the second retrotransposon interspersed element and the internal positive control may be performed simultaneously.

In some embodiments, the internal positive control may comprise a synthetic nucleotide sequence.

In certain embodiments, the process for quantitating human DNA in a sample may comprise providing a primer for the internal positive control, the primer for the internal positive control being selected from the group consisting of a sequence labeled SEQ ID NO: 16, a sequence labeled SEQ ID NO: 17, a sequence labeled SEQ ID NO: 18 and a sequence labeled SEQ ID NO: 19:

```
                                      (SEQ ID NO: 16)
5' AAAGATCCTGCCAACAGGACAGTG 3'

(SEQ ID NO: 17)
5' ACAGACGGTATAGAGACCAATCAG 3'

(SEQ ID NO: 18)
5' GCATAAAGATCCTGCCAACAG 3'

(SEQ ID NO: 19)
5' ACCAAAGTGCTGCAGAAATAC 3'.
```

In certain embodiments, the process for quantitating human DNA in a sample may comprise providing a third probe, the third probe comprising a third moiety capable of fluorescence at a third diagnostic wavelength and a third quencher capable of quenching the third moiety fluorescence, the third probe being targeted to the positive internal control, the Taq polymerase enzyme being further capable of cleaving the third probe to separate the third fluorescent moiety from the third quencher, the third probe having a sequence labeled SEQ ID NO: 20:

```
                                      (SEQ ID NO: 20)
5' AGGCAGAGATTGCACTGCCTTAAAGTGG 3'.
```

In certain embodiments, the first retrotransposon interspersed element and the second retrotransposon interspersed element may independently be one of a SINE target sequence, a LINE (long interspersed elements) target sequence and a SVA target sequence.

In certain embodiments, the first retrotransposon interspersed element may consist of 40 to 150 base pairs, and the second retrotransposon interspersed element may consist of 120 to 400 base pairs.

In certain embodiments, the sensitivity of the DNA quantitation may be in the range of from about 5 pg to about 9 pg.

In certain embodiments, the efficiency of the real time polymerase chain reaction system with respect to each of the first retrotransposon interspersed element and the second retrotransposon interspersed element may be at least about 80%.

In certain embodiments, the process step of using a real time polymerase chain reaction system may include the preparation of standard curves for the quantitation of the first retrotransposon interspersed element and the quantitation of the second retrotransposon interspersed element. The standard curves may each be a plot of a threshold cycle vs. a quantity of DNA, and each may have an $R^2$ value of at least 0.99.

In preferred embodiments, the real time polymerase chain reaction system that is used in the inventive process for quantitating human DNA in a sample may be substantially unreactive to non-primate DNA in the sample.

In certain embodiments, the DNA in a tested sample may have been degraded by one of mechanical means, chemical means and environmental means.

In embodiments of the invention, the real time polymerase chain reaction system may be one of SYBR® Green, TaqMan® and AmpliFluor®.

In certain other embodiments, a process for quantitating total human DNA and male specific DNA in a sample in order to assess the extent of degradation of the DNA therein according to the present invention may comprise the steps of providing a sample to be analyzed, using a real time polymerase chain reaction system to separately quantitate within the sample a male specific DNA sequence, a first retrotransposon interspersed element and a second retrotransposon interspersed element, the male specific DNA sequence being a 90 bp Y-chromosome specific DNA sequence, the first retrotransposon interspersed element being an Alu element, the second retrotransposon interspersed element being an SVA element of the RP gene, and calculating a ratio of an occurrence within the sample of the first retrotransposon interspersed element to an occurrence of the second retrotransposon interspersed element.

In certain embodiments of the process for quantitating total human DNA and male DNA in a sample, the first retrotransposon interspersed element may be one of a SINE target sequence, a LINE target sequence and a SVA target sequence consisting of 40 to 150 base pairs, the second retrotransposon interspersed element may be one of a SINE target sequence, a LINE target sequence and a SVA target sequence consisting of 120 to 400 base pairs, and the male target may be a region of a human Y chromosome DNA containing a 90 base pair sequence which is deleted on a human X-chromosome in an X-Y chromosome homologous region.

In certain embodiments of the process for quantitating total human DNA and male specific DNA in a sample, the first retrotransposon interspersed element may be a target sequence that has about 80 base pairs and is an Alu element of subfamily Yb8, the second retrotransposon interspersed element may be a target sequence that has about 290 base pairs and is an SVA element of the RP gene, and the male specific DNA sequence may be a region of a human Y chromosome DNA containing a 90 base pair sequence which is deleted on a human X-chromosome in an X-Y chromosome homologous region.

In certain embodiments, the process for quantitating total human DNA and male specific DNA in a sample may further comprise providing at least one primer selected from the group consisting of a forward primer labeled SEQ ID NO: 5 and a reverse primer labeled SEQ ID NO: 6 (primers for the Yb8 Alu fragment), providing at least one primer selected from the group consisting of a forward primer labeled SEQ ID NO: 8, a forward primer labeled SEQ ID NO: 11, a forward primer labeled SEQ ID NO: 14, a reverse primer labeled SEQ ID NO: 9, a reverse primer labeled SEQ ID NO: 12, a reverse primer labeled SEQ ID NO: 13 and a reverse primer labeled SEQ ID NO: 15 (primers for the SVA sequence):

```
                                          (SEQ ID NO: 5)
5' GGAAGCGGAGCTTGCAGTGA 3'

(SEQ ID NO: 6)
5' AGACGGAGTCTCGCTCTGTCGC 3'

(SEQ ID NO: 8)
5' TGGGATCCTGTTGATCTGTGACCT 3'

(SEQ ID NO: 9)
5' GATTTGGCAGGGTCATGGGACAAT 3'

(SEQ ID NO: 11)
5' ATGTGCTGTGTCCACTCAGGGTTA 3'

(SEQ ID NO: 12)
5' TTCTTGGGTGTTTCTCACAGAGGG 3'

(SEQ ID NO: 13)
5' ATTCTTGGGTGTTTCTCACAGAGG 3'

(SEQ ID NO: 14)
5' CCAACCCTGTGCTCTCTGAAAC 3'

(SEQ ID NO: 15)
5' TTTGGCAGGGTCATGGGACAA 3',
``` and providing at least one primer selected from the group consisting of a forward primer labeled SEQ ID NO: 25 and a reverse primer labeled SEQ ID NO: 26:

```
                                          (SEQ ID NO: 25)
5' CAATGTG[CTAGGCTCTAGGAATAC 3'

(SEQ ID NO: 26)
5' AAGAGTGTCATGGCTCAAAGAG 3'.
```

In certain embodiments, the process for quantitating total human DNA and male specific DNA in a sample may further comprise providing a probe for the male specific DNA target sequence, the probe having a sequence labeled SEQ ID NO: 27:

```
                                          (SEQ ID NO: 27)
5' AGAGAGTATGACAAACATGGCATGGGC 3'.
```

In certain embodiments, the process for quantitating total human DNA and male specific DNA in a sample may further comprise adding an internal positive control to the sample to form a sample mixture, using the real time polymerase chain reaction system to quantitate the internal positive control within the sample mixture, comparing an expected occurrence within the sample mixture of the internal positive control with an occurrence within the sample mixture of the internal positive control, and using the comparison to determine an extent to which the process was affected by the presence of an inhibitor in the sample.

In certain embodiments, the process for quantitating total human DNA and male specific DNA in a sample may further comprise providing at least one primer selected from the group consisting of a forward primer labeled SEQ ID NO: 21, a reverse primer labeled SEQ ID NO: 22, and a reverse primer labeled SEQ ID NO: 23 (primers for a specifically tailored internal positive control):

```
                                          (SEQ ID NO: 21)
5' GCATAAAGATCCTGCCAACAG 3'

(SEQ ID NO: 22)
5' GCCCGAACTTCCAACACTAT 3'
```

-continued (SEQ ID NO: 23)
5' ATTGTTCCTCCTGCCTGATT 3'.

In certain embodiments, the process for quantitating total human DNA and male specific DNA in a sample may further comprise providing a probe for the positive internal control, the probe having a sequence labeled SEQ ID NO: 24:

(SEQ ID NO: 24)
5' ACAGTGTCAGGCAGAGATTGCACT 3'.

BRIEF DESCRIPTION OF THE FIGURES

The patent or application file contains at least one drawing executed in color. Copies of this patent or patent application publication with color drawing(s) will be provided by the Office upon request and payment of the necessary fee.

A more complete appreciation of the invention, and many of the attendant advantages thereof, will be readily apparent as the same becomes better understood by reference to the following detailed description when considered in conjunction with the accompanying figures, wherein.

DETAILED DESCRIPTION OF THE INVENTION

One embodiment of the present invention is a process for quantitating a human DNA in a sample in order to assess the extent of degradation of the DNA therein, the process comprising the steps of providing a sample to be analyzed, using a real time polymerase chain reaction (PCR) system to separately quantitate within the sample a first retrotransposon interspersed element and a second retrotransposon interspersed element, the first retrotransposon interspersed element being an Alu element, the second retrotransposon interspersed element being an SVA element of the RP gene, and calculating a ratio of an occurrence within the sample of the first retrotransposon interspersed element to an occurrence of the second retrotransposon interspersed element.

In another embodiment of the present invention, the second retrotransposon interspersed element used as a target for quantitation with a real time PCR system may comprise at least three times as many base pairs as are comprised by the first retrotransposon interspersed element.

In another embodiment of the present invention, the first retrotransposon interspersed element may be a target sequence that has about 80 base pairs and is an Alu element of subfamily Yb8, and the second retrotransposon interspersed element may be a target sequence that has about 290 base pairs and is an SVA element of the RP gene.

Figure 3:
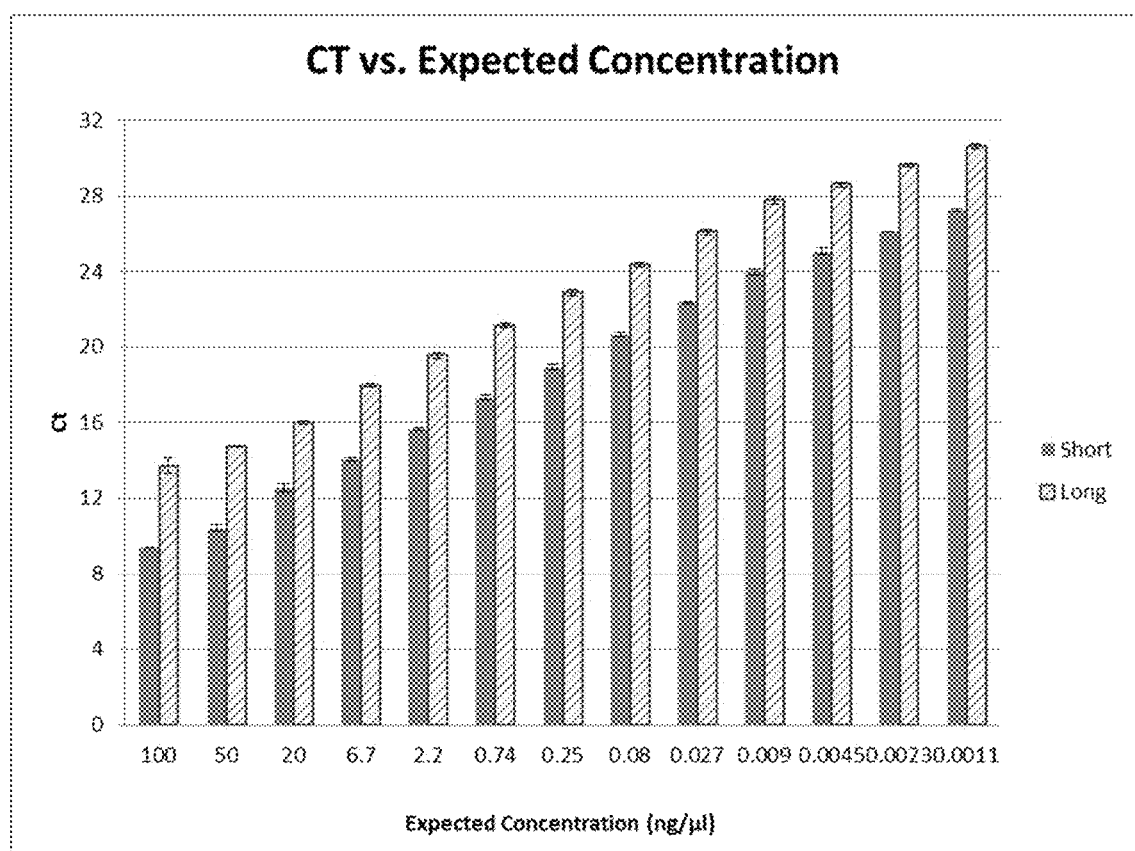
FIG. 3 shows observed threshold cycle values vs. expected concentrations of standards for the gDNA sensitivity standard dilutions.

In another embodiment of the present invention, the inventive processes may be used to determine the extent of admixture of male and female DNA in a test sample. This embodiment is enabled by the existence of a male specific target sequence having about 90 base pairs, the male specific target sequence being deleted on the human X-chromosome in an X-Y chromosome homologous region and being therefore specific to male DNA. As explained in the disclosure of Walker, et al., U.S. Pat. No. 7,405,044 (hereinafter 'Walker'), which is hereby incorporated by reference in its entirety, sex chromosome assays may be designed around a 90 bp deletion on the human X-chromosome in the X-Y homologous region (col. 5, ln 42-44). In FIG. 3 of Walker, the relevant primers are shown in bold font and the chromosome specific probes are shown in lower case underlined font. The deletion starts at X position 89810740 as determined by BLAT (The BLAST like Alignment Tool) (Walker, col. 5, ln 44-47).

The process of an embodiment of the invention may further comprise the steps of providing a first probe, the first probe comprising a first moiety capable of fluorescence at a first diagnostic wavelength and a first quencher capable of quenching the first moiety fluorescence, the first probe being targeted to the first retrotransposon interspersed element, providing a second probe, the second probe comprising a second moiety capable of fluorescence at a second diagnostic wavelength and a second quencher capable of quenching the second moiety fluorescence, the second probe being targeted to the second retrotransposon interspersed element, providing at least one primer that is useful in a real-time polymerase chain reaction system, the system being capable of amplification of a DNA sample, providing a Taq polymerase enzyme capable of catalyzing the formation of a nucleic acid sequence that is complimentary to one present in the sample, the Taq polymerase enzyme being capable both of cleaving the first probe to separate the first fluorescent moiety from the first quencher and of cleaving the second probe to separate the second fluorescent moiety from the second quencher, treating the sample with the first probe and the second probe, amplifying the sample using the at least one primer and the Taq polymerase enzyme by means of the real-time polymerase chain reaction system, illuminating the sample during each real time polymerase chain reaction cycle using an excitation source capable of inducing fluorescence in both the first moiety and the second moiety, measuring the fluorescence emitted from the first moiety and the fluorescence emitted from the second moiety for each real time polymerase chain reaction cycle, determining a threshold cycle number for the first retrotransposon interspersed element and the second retrotransposon interspersed element, and comparing the determined threshold cycle numbers with standard curves (threshold cycle number vs. quantity of DNA) for each of the first retrotransposon interspersed element and the second retrotransposon interspersed element to determine a concentration for each of the first retrotransposon interspersed element and the second retrotransposon interspersed element within the sample.

In another embodiment of the present invention, the goal of determining the extent of degradation present in a DNA sample may be realized by using two independent genomic targets, obtaining quantification of a short DNA fragment having about 79 base pairs and a long DNA fragment having about 290 base pairs in a degraded DNA sample. A multi-copy intra Alu based approach has been developed using these target fragments to quantify human specific DNA in an evidence sample and has been successfully used to obtain DNA quantification with high sensitivity. The use of internal primers to amplify DNA segments including that of an Alu element allows for human specificity as well as high sensitivity when compared to a single copy target.

The method for quantifying the extent of degradation of a human DNA sample relies on the fact that the integrity of the longer insertion sequences will be disrupted at a faster pace than will the integrity of the shorter insertion sequences as the DNA sample degrades in the environment. As the polymerization of the PCR reaction proceeds and the two TaqMan fluorescent probes are cleaved, the respective fluorescent signals are monitored during each PCR cycle, and a threshold cycle, the cycle upon which the signal is first detectable, is determined for each target. Using the log linear relationship between threshold cycle and DNA concentration, a concentration for each target sequence may be determined, and the concentration ratio of the respective target sequences in the DNA sample may be determined. This ratio will be an indication of the extent of degradation of the sample.

In an embodiment of the invention, primers and TaqMan probes are designed using two independent insertion targets. The first is a relatively short (50-150 base pairs) retrotransposon interspersed element insertion, whereas the second is a relatively longer (150-500 base pairs) retrotransposon interspersed element insertion. In other embodiments, the first insertion target has 60-125 base pairs, 75-85 base pairs, or 79 base pairs, and the second insertion target has 200-400 base pairs, 220-320 base pairs, 280-300 base pairs, or 290 base pairs.

The retrotransposon target elements of the present invention must be selected with care. Experimentation with a multiplex composed of Yb8 (80 bp) and Ya5 (250 bp) targets exhibited cross reactivity due to the sequence similarities of these targets. Quantitation values of samples amplified with individual targets Yb8 and Ya5 were discrepant when compared to quantitation values of the same samples amplified in a multiplex reaction containing primers and probes for both the short (Yb8) and long (Ya5) targets in a single amplification due to this cross reactivity. For this study, two forward primers (SEQ ID NO: 1 and SEQ ID NO: 2), a reverse primer (SEQ ID NO: 3) and a probe (SEQ ID NO: 4) corresponding to the Ya5 250 base pair fragment were developed.

In a preferred embodiment of the invention, the shorter retrotransposon interspersed element is a 79 base pair sequence from the Yb8 subfamily of Alu insertions, and the longer retrotransposon interspersed element is a 290 base pair sequence of an SVA element. In this embodiment, a system was developed using the Yb8 Alu sequence of 79 bp in size for the short fragment labeled in 5-carboxyfluorescein (FAM) and the SINE-R region of SVA sequence (H. Wang, et. al, J. Mol. Biol. 354: 994-1007 (2005)) of 290 bp in size labeled in Cy5 for the long target. A synthetic sequence labeled with indocarbocyanine Cy3 dye was also used as an internal positive control (IPC) to assess the presence or absence of inhibitors in the sample. A second version of this embodiment includes a fourth, male DNA specific, target. In this system, the 79 bp Yb8 fragment was labeled in 2',7'-dimethoxy-4',5'-dichloro-6-carboxyfluorescein (JOE), the 290 bp SVA fragment was labeled in indocarbocyanine Cy5, the male DNA target sequence on the Y chromosome is a 76 bp fragment and was labeled in FAM, and the IPC sequence was labeled in Cy3. In other embodiments making use of similar approaches, other multi-copy retrotransposons, such as Long Interspersed Elements (LINE), may also be used.

In some embodiments, use of a multi-copy target, two different size sequence markers along with a synthetic target as an Internal Positive Control (IPC) may provide an additional assessment for the presence of PCR inhibitors in the test sample. This is an important way of determining whether the sample matrix may be altering the operation of the test by providing assurance that the expected fluorescence ratios are obtainable under the test conditions.

The present invention will now be described more fully with reference to the accompanying drawing (FIG. 1), in which an exemplary embodiment of the invention is shown.

Figure 1:
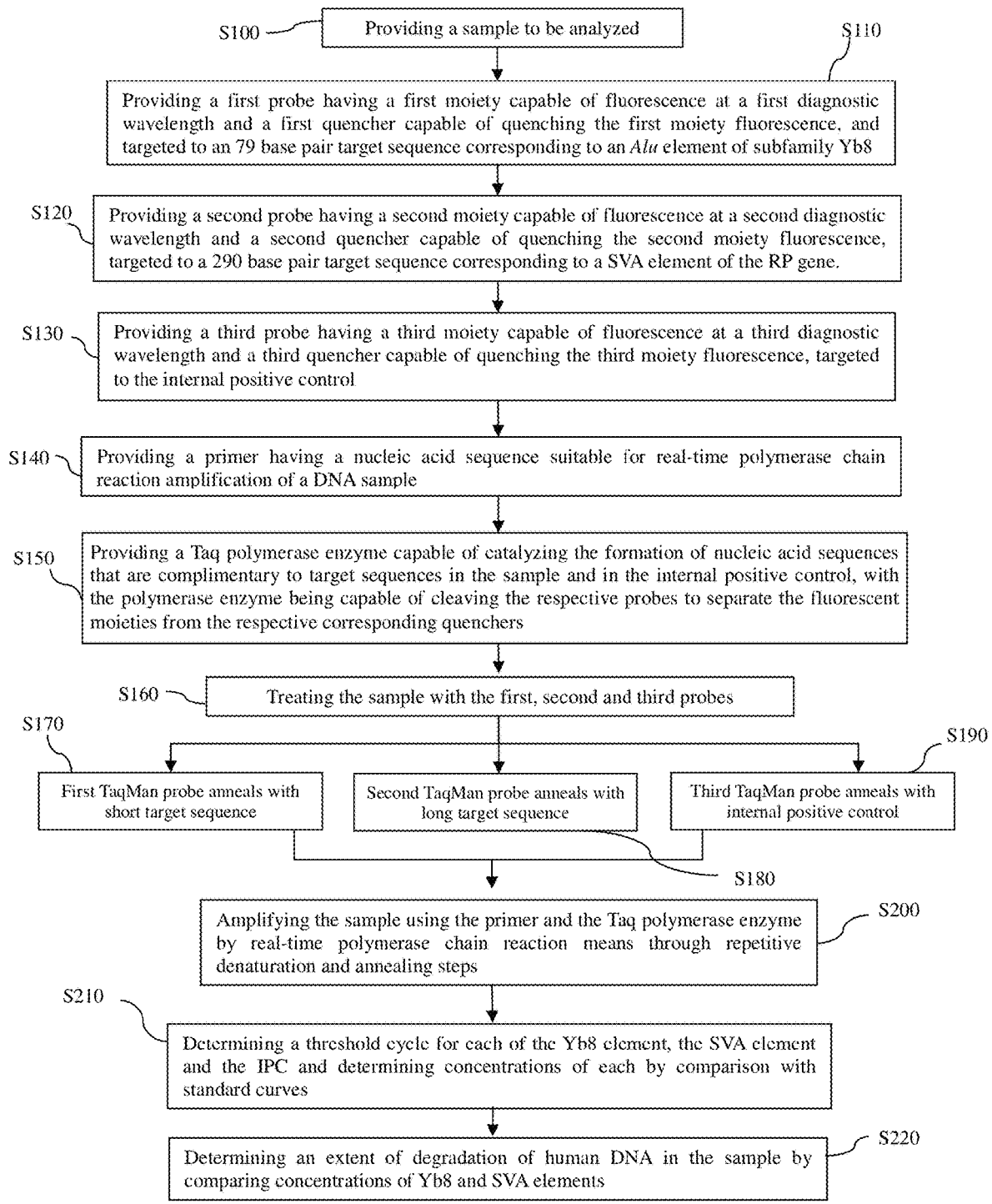
FIG. 1 is a flowchart illustrating a process for determining the extent of environmental degradation of a human DNA sample according to the present invention.

As shown in FIG. 1, a DNA sample (S100) is paired with three TaqMan probes (S110, S120, and S130), a real-time PCR primer (S140) and a Taq polymerase enzyme (S150), the Taq polymerase enzyme being capable of cleaving the TaqMan probes, separating each fluorescent moiety from its respective quencher. In the TaqMan procedure, the sample is treated with the first TaqMan probe, the second TaqMan probe and the third TaqMan probe (S160), the TaqMan probes anneal with one of the complimentary nucleic acid strands (S170, S180, S190), the sample is amplified using a standard real-time PCR technique, and the TaqMan probes corresponding to the target elements are cleaved to separate the three fluorophores from their respective quenchers during repetitive denaturation and annealing steps (S200). Illuminating the sample during each PCR cycle causes the fluorophores from both types of cleaved TaqMan probes to fluoresce. A threshold cycle for each of the Yb8 element, the SVA element and the internal positive control may then be determined, and concentrations of each of these may then be determined by comparison with standard curves (S210). The ratio of concentrations of the Yb8 element and the SVA element may be related to the extent of environmental degradation in the original DNA sample (S220). Comparison of an expected concentration of the internal positive control with a concentration obtained for the internal positive control provides information about the extent to which PCR inhibitors may be present in the sample.

The latter process is versatile and may be modified to provide additional useful information. One of skill in the art may readily envision modification of the above procedure to include a fourth probe corresponding to the male specific DNA target described above.

Precision and sensitivity studies have indicated that the process of the preferred embodiment of the present invention has a sensitivity threshold in the range of about 5 pg to about 9 pg, similar to sensitivities reported for other Alu-based quantification systems. The amount of synthetic IPC target may be adjusted to provide reproducible threshold cycle (Ct) values in the range from 18 to 22 cycles for samples with no inhibition.

Estimated quantitation for both 79 bp and 290 bp fragments obtained using the new primers and TaqMan probes were compared with STR analysis results obtained from DNA samples degraded using sonication, DNAse I and environmental degradation, and the correlation indicates that the process of the preferred embodiment of the present invention is a reliable one for determining the extent of degradation of a human DNA sample. In all instances, the STR results mirrored the degradation ratios calculated by this duel target quantification assay.

The present invention provides a quantification system that accurately assesses the quality of human DNA present in a forensic sample. Results demonstrate the preferred embodiment of the present invention to be specific to higher primates, sensitive down to 5-9 pg of DNA, reproducible, and a useful tool for assessing degradation in a biological sample. A DNA based qualitative/quantitative/inhibition assessment system that accurately predicts the status of a biological sample may serve as a valuable tool for deciding which DNA test kit to utilize when processing forensically compromised samples for DNA testing.

EXAMPLES

Preferred embodiments of the present invention may be better understood through the following characterizations of experimental methods, conditions, accuracy and precision of the process of the present invention and the associated examples that follow.

Example 1: Primers and Probes

Primers and probes that are useful in the described embodiments are shown in Table 1. An intra RE primer design was used to target a Yb8 Alu sequence of 79 bp in size for the "short" fragment as well as a sequence in the SINE-R region of SVA of 290 bp in size for the "long" target. An internal positive control (IPC) to assess the presence or absence of inhibitors in the sample was studied as well. IPC target synthetic sequences of 92 bp, 158 bp, 172 bp, and 192 bp were studied. Inhibition studies using inhibitors commonly found in forensic samples were performed on the 92 bp, 158 bp, and 172 bp IPC target sequences.

Two systems were developed: one three target system containing the Yb8 "short" Alu fragment labeled in FAM, the SVA "long" fragment labeled in Cy5, and a synthetic sequence labeled with Cy3 dye used as the IPC. A second system comprised of four targets was developed incorporating a male specific DNA target sequence to detect male DNA in the sample. In this system, the "short" 79 bp Yb8 fragment was labeled in JOE, the "long" 290 bp SVA fragment was labeled in Cy5, the male specific DNA target sequence on the Y chromosome is a 76 bp fragment and was labeled in FAM, and the IPC sequence was labeled in Cy3.

Figure 15:
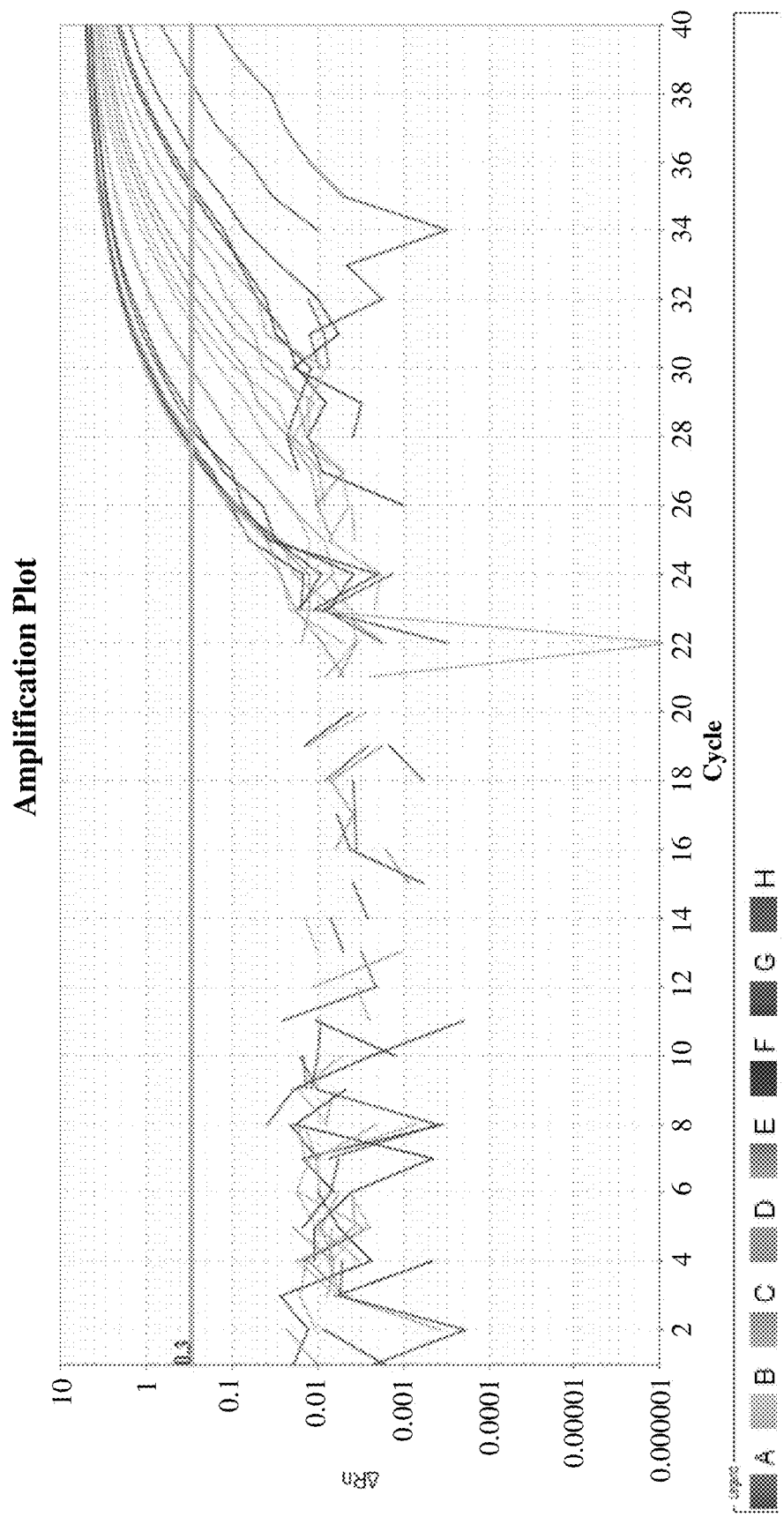
FIG. 15 shows the amplification plot of the Y chromosome target sequence in a single-plex reaction.

Primers and probes were designed for the Y chromosome marker to provide specificity to the Y chromosome target by placing the probe within the 90 bp X chromosome deletion. Single-plex reactions were run to verify the correct products formed. Because the copy number of this target sequence is not as high as the Yb8 or SVA copy number, a higher number of cycles were needed to produce amplification products. In a single reaction, 40 cycles produced a standard curve with 126% efficiency. See FIG. 15 for the real-time amplification plot of the single-plex Y reactions.

TABLE 1

Primer sequences

| Target Name | Primer or Probe Name | Primer Sequence | Sequence ID |
|---|---|---|---|
| Ya5 | Forward-1 | TCACGCCTGTAATCCCAGCACTT | SEQ ID NO: 1 |
|  | Forward-2 | ACGCCTGTAATCCCAGCACTTTG | SEQ ID NO: 2 |
|  | Reverse | TCTGTCGCCCAGGCTGGAGT | SEQ ID NO: 3 |
|  | Probe | ATCACGAGGTCAGGAGATCGAGACCAT | SEQ ID NO: 4 |
| Yb8 | Forward | GGAAGCGGAGCTTGCAGTGA | SEQ ID NO: 5 |
|  | Reverse | AGACGGAGTCTCGCTCTGTCGC | SEQ ID NO: 6 |
|  | Probe | AGATTGCGCCACTGCAGTCCGCAG | SEQ ID NO: 7 |
| SVA | Forward | TGGGATCCTGTTGATCTGTGACCT | SEQ ID NO: 8 |
|  | Reverse | GATTTGGCAGGGTCATGGGACAAT | SEQ ID NO: 9 |
|  | Probe | AAGGGCGGTGCAAGATGTGCTTTGTT | SEQ ID NO: 10 |
|  | Forward-Q2F | ATGTGCTGTGTCCACTCAGGGTTA | SEQ ID NO: 11 |
|  | Reverse-Q2R1 | TTCTTGGGTGTTTCTCACAGAGGG | SEQ ID NO: 12 |
|  | Reverse-Q2R2 | ATTCTTGGGTGTTTCTCACAGAGG | SEQ ID NO: 13 |
|  | Forward-Q3F | CCAACCCTGTGCTCTCTGAAAC | SEQ ID NO: 14 |

TABLE 1 -continued

Primer sequences

| Target Name | Primer or Probe Name | Primer Sequence | Sequence ID |
|---|---|---|---|
| | Reverse-Q3R | TTTGGCAGGGTCATGGGACAA | SEQ ID NO: 15 |
| | Forward (90) | AAAGATCCTGCCAACAGGACAGTG | SEQ ID NO: 16 |
| | Reverse (90) | ACAGACGGTATAGAGACCAATCAG | SEQ ID NO: 17 |
| IPC | IPCr7-Forward (158) | GCATAAAGATCCTGCCAACAG | SEQ ID NO: 18 |
| | IPCr7-Reverse (158) | ACCAAAGTGCTGCAGAAATAC | SEQ ID NO: 19 |
| | Probe | AGGCAGAGATTGCACTGCCTTAAAGTGG | SEQ ID NO: 20 |
| IPC-M | Forward | GCATAAAGATCCTGCCAACAG | SEQ ID NO: 21 |
| | Reverse-172 bp | GCCCGAACTTCCAACACTAT | SEQ ID NO: 22 |
| | Reverse-192 bp | ATTGTTCCTCCTGCCTGATT | SEQ ID NO: 23 |
| | Probe | ACAGTGTCAGGCAGAGATTGCACT | SEQ ID NO: 24 |
| Y chromo-some | Forward | CAATGTG[CTAGGCTCTAGGAATAC | SEQ ID NO: 25 |
| | Reverse | AAGAGTGTCATGGCTCAAAGAG | SEQ ID NO: 26 |
| | Probe | AGAGAGTATGACAAACATGGCATGGGC | SEQ ID NO: 27 |

Optimization of PCR conditions was carried out as described in Examples 2-5.

Example 2: Number of Cycles

The manufacturer recommendation for the QPCR Multiplex master mix is: 95° C. for 10 minutes followed by 40 cycles of 95° C. for 15 seconds and 60° C. for 60 seconds. To test the number of cycles that would be optimal for the duel target quantification assay, the number of cycles was varied. Tests of 40 cycles and 32 cycles were carried out, and PCR efficiency values were examined. The results showed higher PCR efficiencies when 32 cycles were used.

Example 3: Annealing and Denaturation Times

The manufacturer recommendation for PCR conditions is: 95° C. for 10 minutes followed by 40 cycles of 95° C. for 15 seconds and 60° C. for 60 seconds. To test which PCR conditions would be optimal for the InnoQuant Quantification Kit™ (InnoGenomics Technologies, LLC), denaturation and annealing times were varied. Four annealing times were tested: 45, 60, 70, and 120 seconds; and two denaturation times were tested: 15 seconds and 30 seconds. PCR efficiency, $R^2$ values, and standard deviation of the triplicate quantitation values (three DNA extracts were run in triplicate) were examined.

Results indicate that, for the preferred embodiment of the present invention, the longer second annealing time yields slightly improved PCR efficiencies and lower standard deviation of the triplicate quantification values than was achieved at shorter annealing times. A longer annealing time also provides more time for the enzyme to function properly with the longer targets. Additionally, results indicate that a 30 second denaturation time significantly decreases the $R^2$ value of the standard curve of both targets relative to that attained with the 15 second denaturation time. Therefore, the 15 second denaturation time and 120 second annealing time were selected for use with the preferred embodiment.

Example 4: Annealing Temperature

Three annealing temperatures were tested: the manufacturer-recommended 60° C., 61° C., and 62° C. Efficiencies, $R^2$ values, and standard deviation of the sample triplicates were analyzed. The results are shown in Table 2.

TABLE 2

Annealing temperature runs

| Run date | Conditions | Yb8 Efficiency | Yb8 $R^2$ | Yb8 SD | SVA Efficiency | SVA $R^2$ | SVA SD |
|---|---|---|---|---|---|---|---|
| Oct. 30, 2012 | SVA/Yb8 0.3 IPC 0.2 stds at 20 ng 60° C. Annealing temp | 88% | 0.998 | 0.29 | 87% | 0.998 | 0.39 |
| Oct. 30, 2012 | SVA/Yb8 0.3 IPC 0.2 stds at 20 ng 61° C. Annealing temp | 95% | 0.993 | 0.16 | 85% | 0.994 | 0.24 |

TABLE 2-continued

Annealing temperature runs

| Run date | Conditions | Yb8 Efficiency | Yb8 R² | Yb8 SD | SVA Efficiency | SVA R² | SVA SD |
| --- | --- | --- | --- | --- | --- | --- | --- |
| Oct. 31, 2012 | SVA/Yb8 0.3 IPC 0.2 stds at 20 ng 61° C. Annealing temp | 91% | 0.998 | 0.27 | 82% | 0.997 | 0.22 |
| Oct. 31, 2012 | SVA/Yb8 0.3 IPC 0.2 stds at 20 ng 62° C. Annealing temp | 86% | 0.996 | 1.51 | 84% | 0.997 | 0.98 |

A 62° C. annealing temperature exhibited wide standard deviation of the sample triplicates and a relatively low efficiency of the Yb8 target. Based on these results, an annealing temperature of 61° C. was selected due to the relatively high efficiency of the Yb8 target. The final PCR conditions selected for the preferred embodiment were as follows: 95° C. for 10 min, 32 cycles of: 95° C. for 15 seconds, 61° C. for 70 seconds.

Example 5: Primer and Probe Concentrations

The two targets were tested individually to determine the best primer and probe concentrations. Once a determination was made from the individual runs, the two targets were multiplexed, and varying concentrations of each in combination were tested. At least two separate runs were performed for each parameter to ensure reproducibility of the results. Primer and probe concentrations were varied for the SVA and Yb8 targets. (The IPC primer/probe concentrations remained fixed at 150 nM final concentration in the reaction [0.2 µL put into reaction], and IPC template DNA amount remained fixed at 4.5 pg.) The average of the standard curve efficiencies and $R^2$ values, and standard deviation of the sample quantities (tested in triplicate) were examined. Based on the results, a final primer concentration of 0.3 µM (0.6 µl of a 10 µM stock) for SVA and 0.25 µM (0.5 µl of a 10 µM stock) for Yb8 in a total reaction volume of 20 µl was selected.

Example 6: Primer Cross Reactivity

Figure 2A:
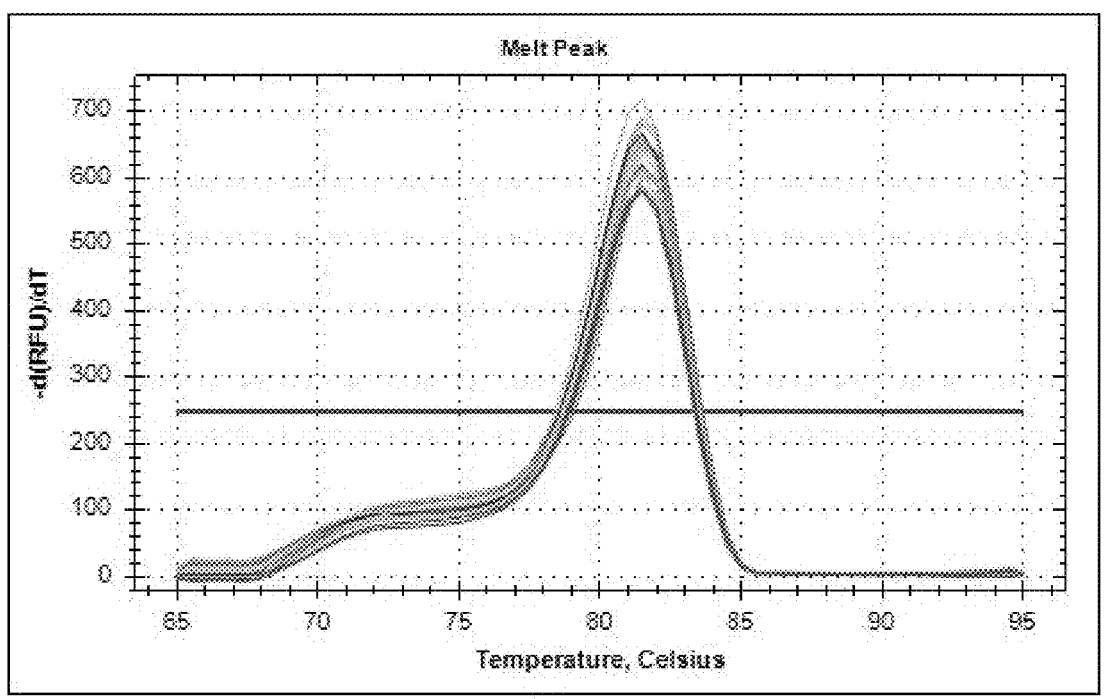
FIGS. 2A and 2B show melt curve analyses for the Yb8 and SVA target, respectively.
Figure 2B:
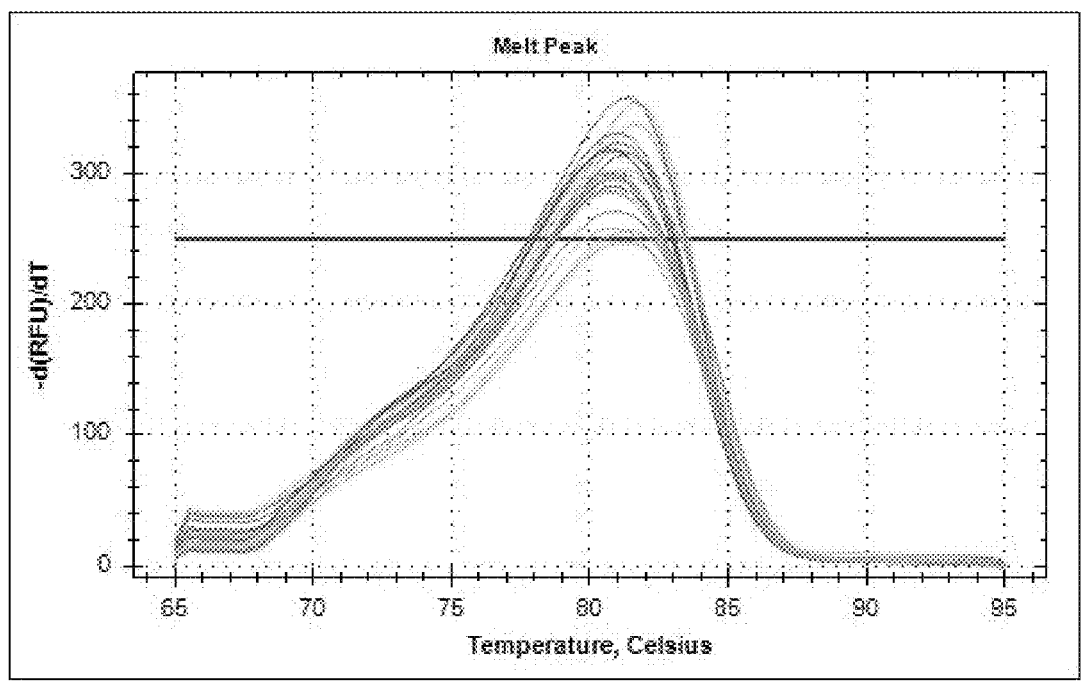

To verify the accuracy of the quantity obtained from each target and to rule out any cross reactivity between primers, a melt curve analysis and amplification artifacts from reactions containing the short target forward primer and the long target reverse primer were examined by fragment analysis. Melt curves exhibit the presence of a single peak for each of the Yb8 and SVA reactions, as expected. A slightly broad base was observed for both targets, indicating the presence of primer dimers. FIGS. 2A and 2B show melt curve analyses for the Yb8 and SVA targets respectively.

Fragment analysis confirmed the presence of the targeted fragment for each target as well as the absence of any artifacts resulting from cross reactivity between the primers (see Table 3). Some primer dimers were observed and one artifact at ~67 bp was also observed. Overall, the results of the melt curve analysis and the fragment analysis confirm the presence of the targeted fragments and the absence of artifacts.

TABLE 3

Fragment Analysis Results

| | Peaks Observed (size in base pairs) | | |
| --- | --- | --- | --- |
| | Primer Dimer | Expected Peak | Artifact |
| SVAF/R + Yb8F/R | 50 bp & 59/65 bp | 73 + 290 | |
| SVAF/R + Yb8R | ~50 bp | 290 | 67 |
| Yb8F/R + SVAR | 59/65 bp | 73 | |
| SVAF + Yb8R | | No peaks observed | 67 |
| Yb8F + SVAR | | No peaks observed | |

Example 7: Multiplex Sensitivity

The sensitivity study was designed such that a given set of measurements (threshold cycle, or $C_t$ value) could be evaluated at various input ranges using a log-linear relationship across the input amounts and to establish the lowest levels of sensitivity where the log-linear relationship was lost. For the Sensitivity Study, one plate of samples, standards, and negative controls, that were quantified with the InnoQuant Quantification Kit™ and run on an Applied Biosystems 7500 Real-Time PCR System, were evaluated using the HID Real-Time PCR Analysis Software v 1.1. Three serial dilutions of the standards (designated as STD1, STD2, and STD3) were made using Teknova DNA dilution buffer (10 mM Tris-0.1 mM EDTA) and run on the trays in duplicate. Different combinations of the DNA standards from the 2 quantification plates were used to determine the average $C_T$ and quantity of each standard when designated as "unknown". An extension of the DNA standard dilution STD3 was made two quantities above the highest standard and two quantities below the lowest standard at 100 ng/µl, 50 ng/µl, 0.0045 ng/µl and 0.0023 ng/µl concentrations. Using the different DNA standard configurations, an average $C_T$ and quantity were calculated for each standard labeled as an unknown. The $C_T$ vs. DNA quantity (ng/µl, on a logarithmic scale) for the unknown standard samples were plotted to demonstrate the linearity of the system. The same analysis was performed on other samples run during this validation, including the 100 ng/µl, 50 ng/µl, 0.0045 ng/µl and 0.0023 ng/µl extensions of the standard samples.

Example 8: Accuracy, Precision, Sensitivity and Linearity of DNA Determinations Table 4 shows the average quantity and $C_T$ values determined for the standards dilutions using the different combinations of the standard curves run on the plate. FIG. 3 is the graphical representation of the data in Table 4. Results demonstrate that the InnoQuant Kit™ consistently detected all samples at as little as 2.3 pg of total input DNA. As the DNA concentration goes beyond the concentrations of the standard curve (20 ng/ul to 0.009 ng/ul), the variation from the expected quantities increases, and linearity is lost to an extent. However, these variations are minimal and would not have affected the ability to obtain full DNA profiles; the increase variation can be expected with the lower concentrations (stochastic amplification effects). The average fold change between the quantity and the expected quantity is 1.13 for the short target and 1.07 for the long target, when all the dilutions are included. A 1.13 fold change of the human average quantity value would result in an approximate 13% variation in the quantity of the human quantifications. The two targets are amplified in a single reaction, but the small target quantity demonstrated slightly higher variation at several of the sensitivity dilutions. When examining the samples within the concentrations of the standard curve (20 ng/ul to 0.009 ng/ul), the fold changes decrease to an average of 1.04 for the short target and 1.06 for the long target. These fold changes in quantities would not significantly affect the Relative Fluorescent Units (RFU) seen in the electropherograms and are due to stochastic amplification effects. Higher fold differences were observed outside of the standard curve range and would be expected with the amount of template amplified.

The results for the 0.0045 ng and 0.0023 ng sample demonstrate the sensitivity of this dual target quantification assay to detect DNA samples below 9 pg. The reproducibility of such values is influenced by stochastic amplification effects associated with low template amplifications. The stochastic amplification effects can be seen in human or male amplifications and not necessarily at the same time. Samples at or near the ends of the standard curve are more susceptible to changes in slope of the standard curve. When samples quantify greater than 20 ng, the laboratory may consider diluting and re-quantifying samples to assure appropriate quantification value.

calculated using the short target (Yb8) of this dual target assay. If differences were observed, in all instances, Quantifiler® human values were higher than dual target quantification assay values. These differences are attributed to differences in the DNA standards and differences in amplicon length (62 bp in Quantifiler® vs. 80 bp in dual target quantification assay system).

Figure 4:
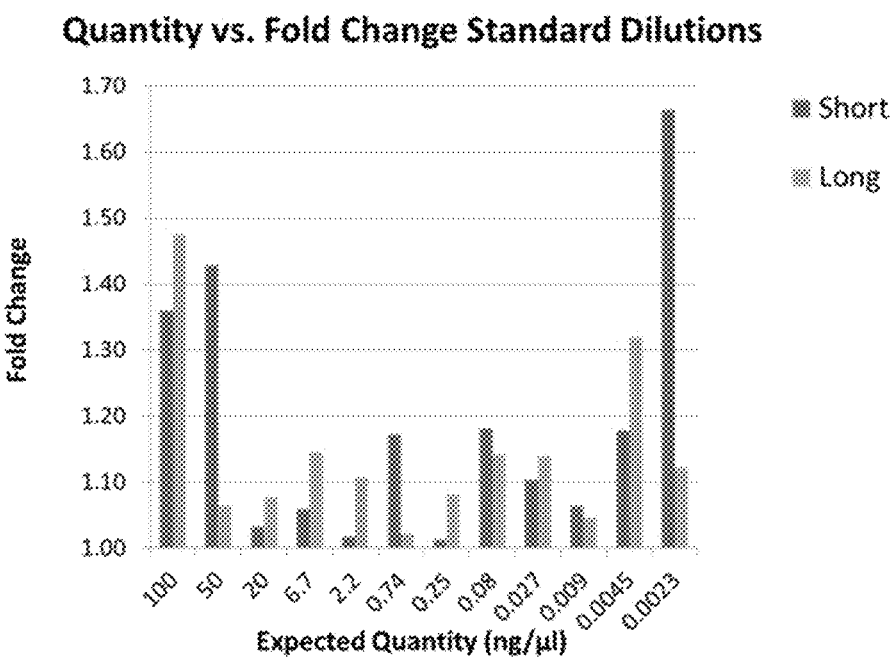
FIG. 4 shows fold changes between each replicate of the standard dilutions, based on at least 34 readings at each DNA concentration.
Figure 5A:
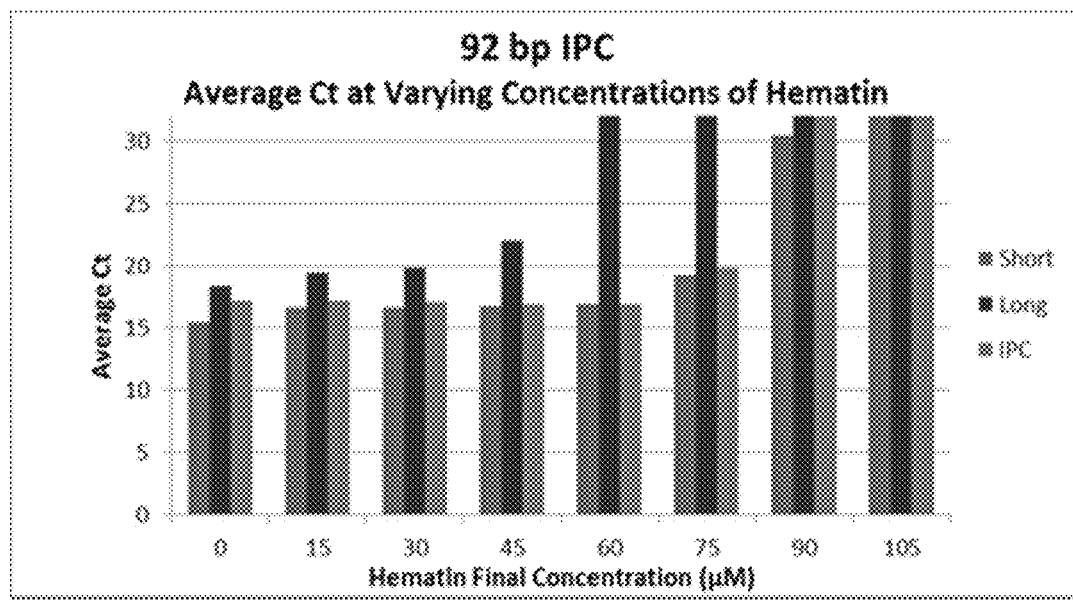
FIGS. 5A and 5B show observed threshold cycle values vs. hematin concentration for hematin inhibited samples using the 92 bp and the 172 bp internal positive controls (IPC's), respectively.
Figure 5B:
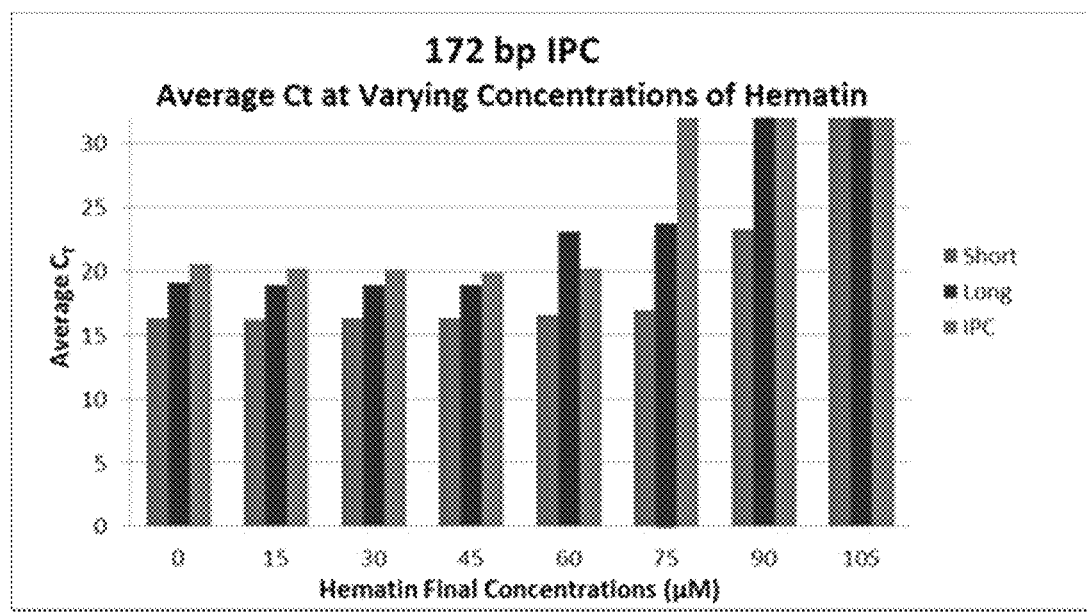
Figure 6A:
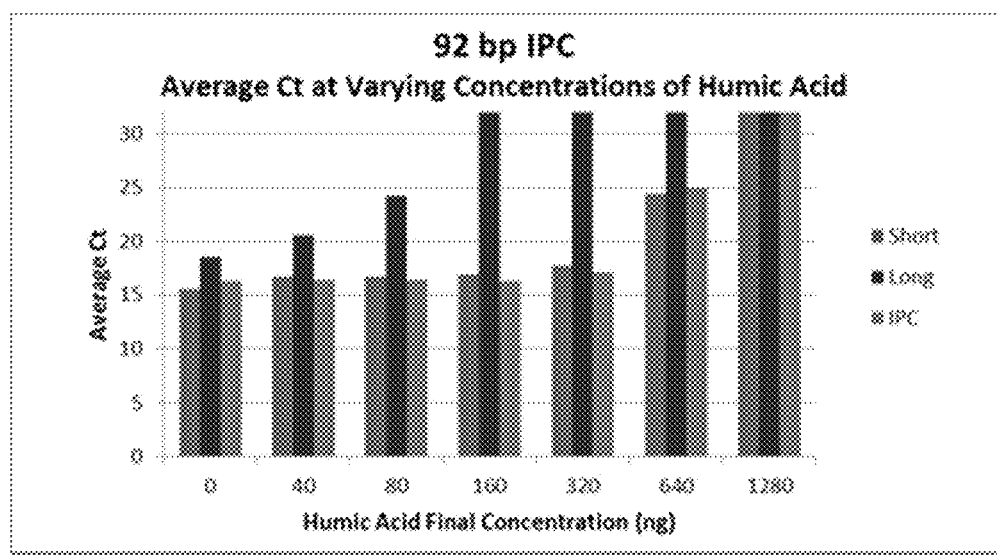
FIGS. 6A and 6B show observed threshold cycle values vs. humic acid concentration for humic acid inhibited samples using the 92 bp and the 172 bp IPC's, respectively.
Figure 6B:
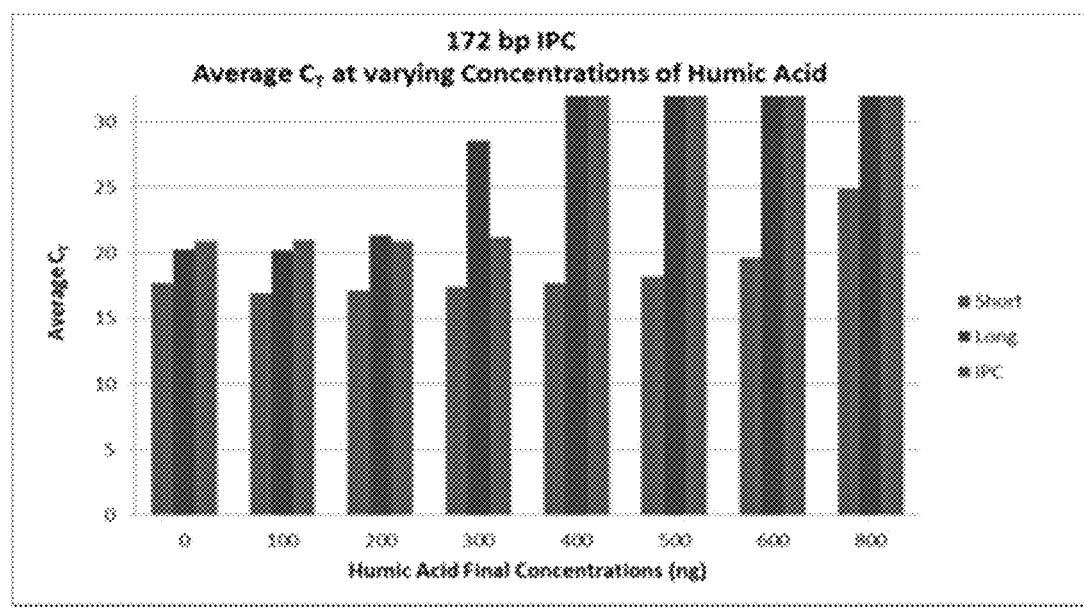
Figure 7:
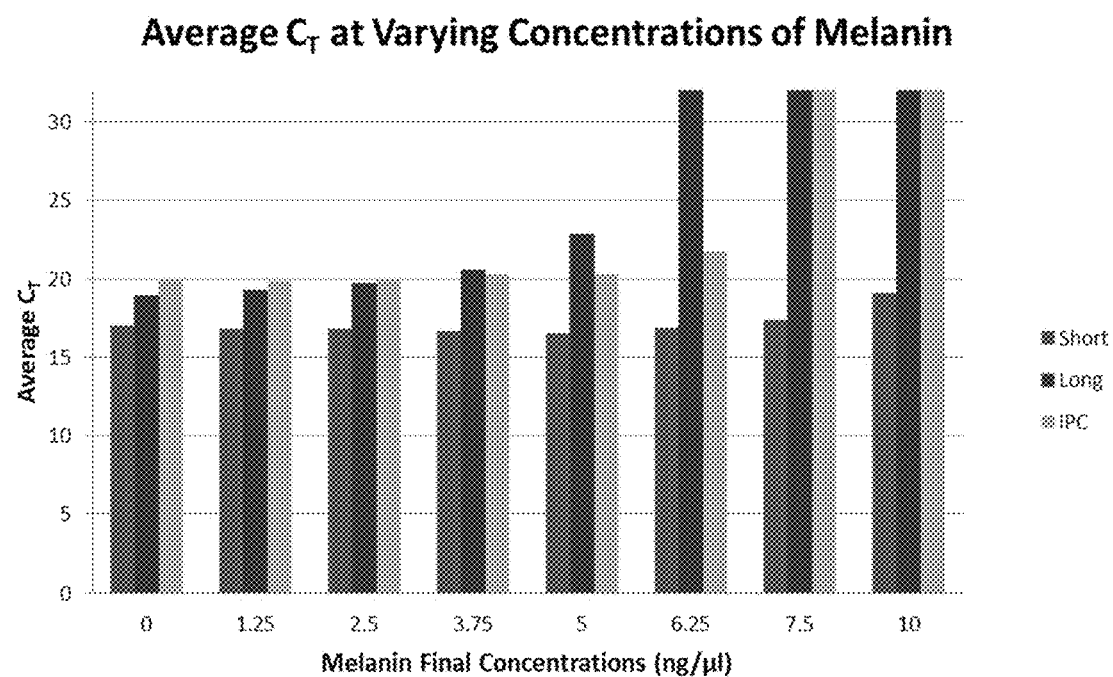
FIG. 7 shows the observed threshold cycle values vs. melanin concentration for melanin inhibited samples using the 172 bp IPC.

To test the reproducibility of the system across various DNA concentrations, the sensitivity data was examined for fold changes in concentration between the replicates. FIG. 4 shows the results of the fold changes between each replicate of the standard dilutions (at least 34 readings from each concentration). Results indicate that between the concentrations of the standards (20 ng to 9 pg), fold changes are all less than 1.20, which is equivalent to a 20% variation. As the concentrations go above or below the optimal range, fold changes increase, as expected.

Example 10: Effects of Inhibition

Varying concentrations of humic acid and hematin were used to inhibit samples using the 92 base pair IPC sequence and the 172 bp IPC sequence. Varying concentrations of melanin were used to inhibit samples using the 172 bp IPC sequence. This inhibitor was selected due to the prevalence of hair samples in forensic casework. The samples were quantified with the InnoQuant Quantification Kit™, and the $C_t$ values of the Yb8, SVA, and IPC targets were evaluated. FIGS. 5A, 5B, 6A, 6B and 7 show the results for the inhibitors tested.

A comparison of the $C_t$ values between the two sized IPC targets for the same inhibitor concentrations shows the 172 bp target is inhibited more readily, as expected due to its larger size. Results show a gradual increase in $C_t$ as the concentration of the inhibitor increases with both the 92 and the 172 bp targets. With the 92 bp IPC, it is observed that the Yb8 and IPC targets have similar reactions to inhibitors, and are affected at approximately the same level of inhibitor. SVA has a higher sensitivity to inhibitors and is the first

TABLE 4

Average quantity and Ct values for the standard dilutions and the gDNA dilutions

| Sample Name (Expected Concentration) ng/ul | Observed Yb8 | | | Observed SVA | | |
|---|---|---|---|---|---|---|
| | Ave. CT | Ave. Qty | Fold Change | Ave. CT | Ave. Qty | Fold Change |
| 100 | 9.41 | 153.8067 | 1.54 | 13.73 | 104.7562 | 1.05 |
| 50 | 10.43 | 78.2061 | 1.56 | 14.78 | 50.5777 | 1.01 |
| 20 | 12.57 | 18.7944 | 1.06 | 16.00 | 22.4396 | 1.12 |
| 6.7 | 14.08 | 6.7444 | 1.01 | 17.96 | 6.1197 | 1.09 |
| 2.2 | 15.66 | 2.3506 | 1.07 | 19.54 | 2.1496 | 1.02 |
| 0.74 | 17.33 | 0.7682 | 1.04 | 21.13 | 0.7456 | 1.01 |
| 0.25 | 18.93 | 0.2625 | 1.05 | 22.90 | 0.2318 | 1.08 |
| 0.08 | 20.64 | 0.0836 | 1.05 | 24.38 | 0.0866 | 1.08 |
| 0.027 | 22.34 | 0.0268 | 1.01 | 26.09 | 0.0278 | 1.03 |
| 0.009 | 24.00 | 0.0088 | 1.02 | 27.78 | 0.0091 | 1.02 |
| 0.0045 | 25.09 | 0.0043 | 1.06 | 28.61 | 0.0052 | 1.16 |
| 0.0023 | 29.66 | 0.0021 | 1.09 | 29.66 | 0.0026 | 1.13 |
| Average Yb8 Fold Change | | | 1.13 | Average SVA Fold Change | | 1.07 |

Example 9: Concordance and Reproducibility

Nineteen samples were quantified using this dual target assay, the preferred embodiment of the invention, and the Quantifiler® Human kit from Life Technologies. Quantifiler® human DNA concentrations averaged 140% of those target to be affected. In contrast, the 172 bp IPC target sequence is the first target of the three to be affected by inhibition. The 172 bp IPC target tracks with the SVA target, as both are affected similarly as the concentration of the inhibitor increases, whereas Yb8 is the last target to be affected as the concentration of the inhibitor increases. Due to the improved correlation of the 172 bp IPC with the short and long targets, this was selected to be incorporated into the multiplex.

As with the other inhibitors tested, results of the melanin inhibitor show a gradual increase in the Ct of all three targets as the concentration of the inhibitor increases. In the case of melanin, the SVA long target is the first of the three targets to be affected, possibly due to a different mechanism of inhibition.

Example 11: Effects of Degradation on the Determination of DNA

Figure 8:
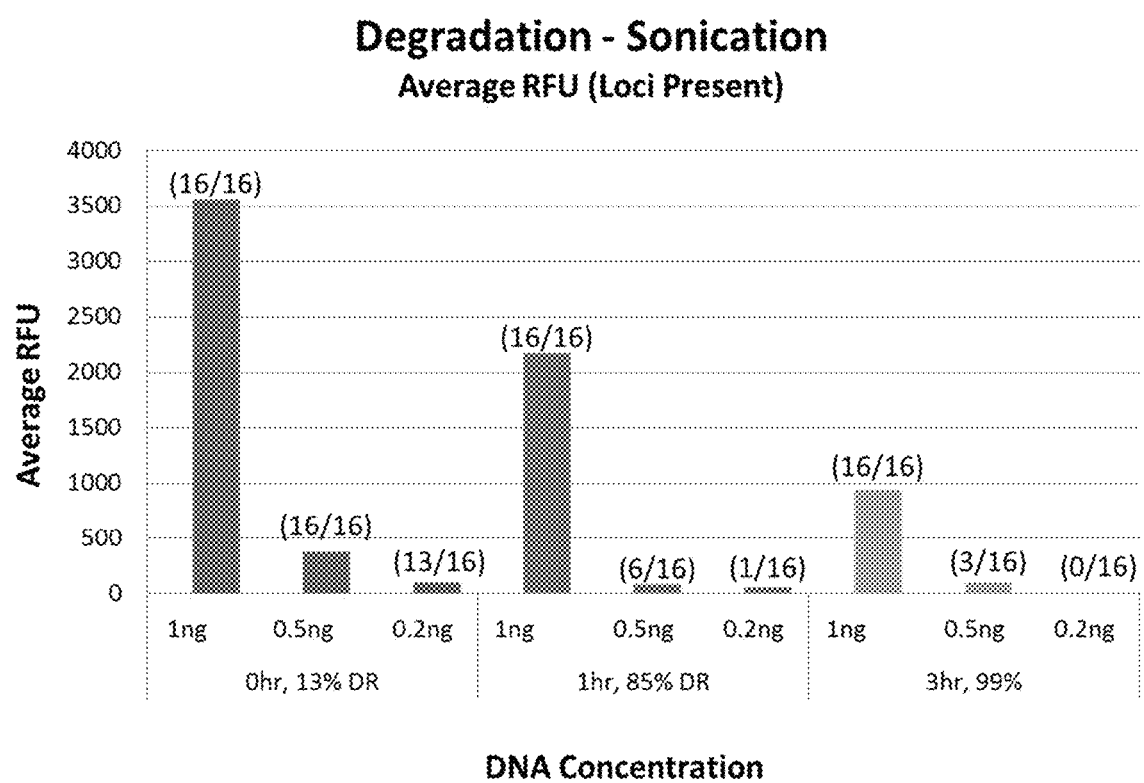
FIG. 8 shows the effects of mechanical degradation by sonication as plots of relative fluorescence units across three different DNA concentrations without degradation and for two degradation times.
Figure 9:
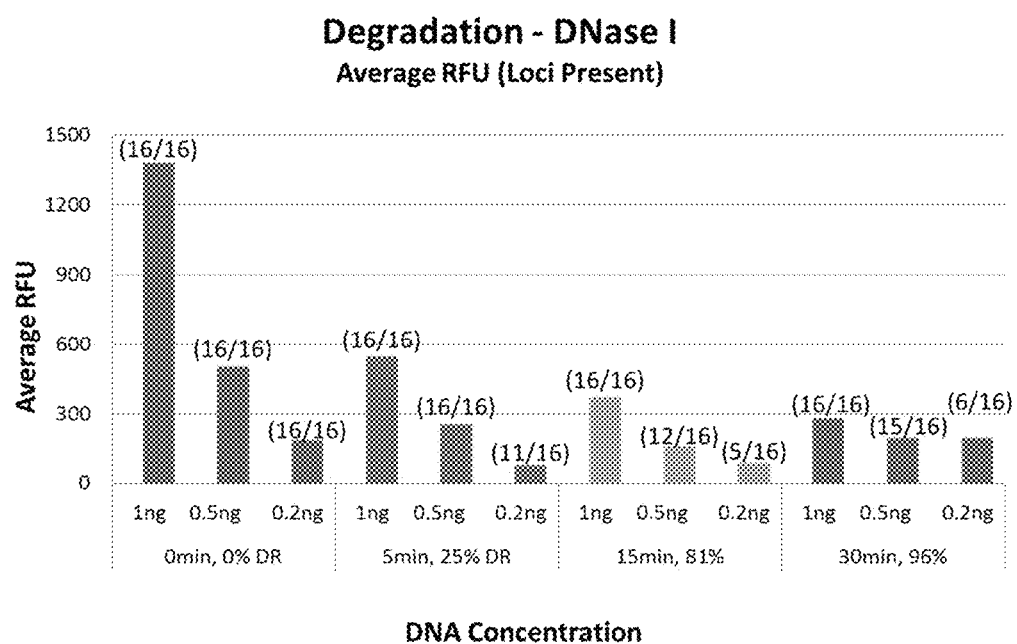
FIG. 9 shows the effects of chemical degradation by the action of DNase I as plots of relative fluorescence units across three different DNA concentrations without degradation and for three degradation times.
Figure 10:
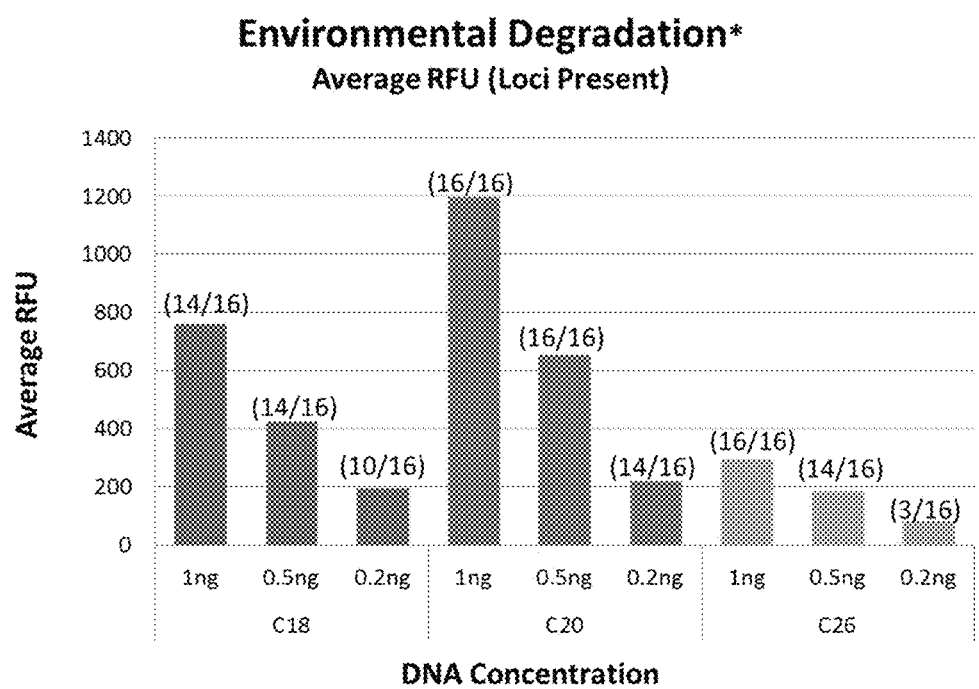
FIG. 10 shows the effects of environmental degradation by the action of ambient heat and humidity for a period of five years as plots of relative fluorescence units across three different DNA concentrations for three degradation times.

Degradation studies were performed to assess the utility of this duel target quantification assay, the preferred embodiment of the present invention, with degraded samples. The experiments were designed to assess three types of degradation: mechanical (via sonication), chemical (via DNase I) and environmental degradation (samples placed in the outside elements [heat, humidity] for a period of 5 years). Degradation ratios based on the observed quantities of the long and short targets were expressed as a percentage=(1−[Long Qty/Short Qty])*100. Results are shown in FIGS. 8 through 10.

Figure 11:
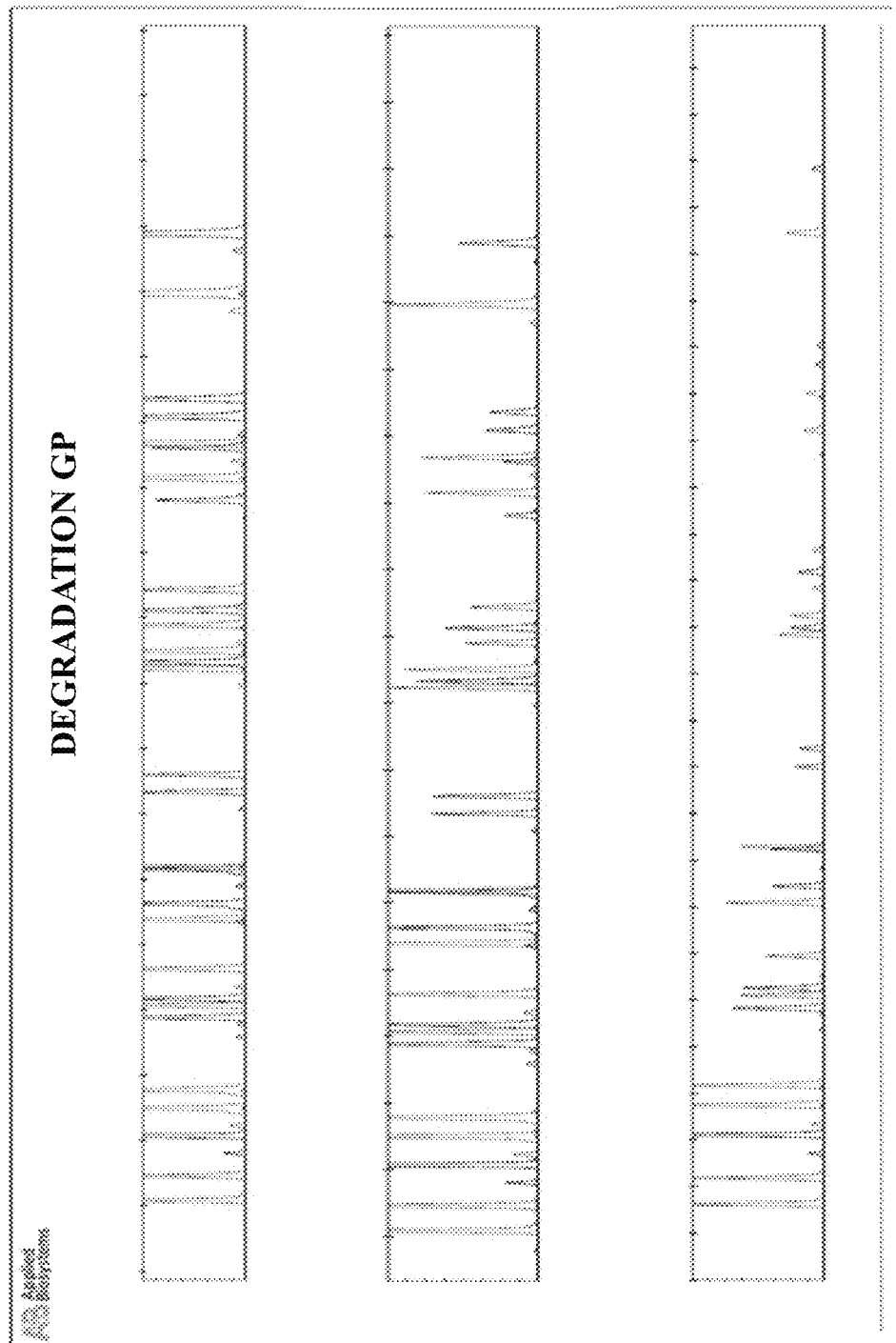
FIG. 11 shows STR results for 1 ng targeted sonicated samples.
Figure 12:
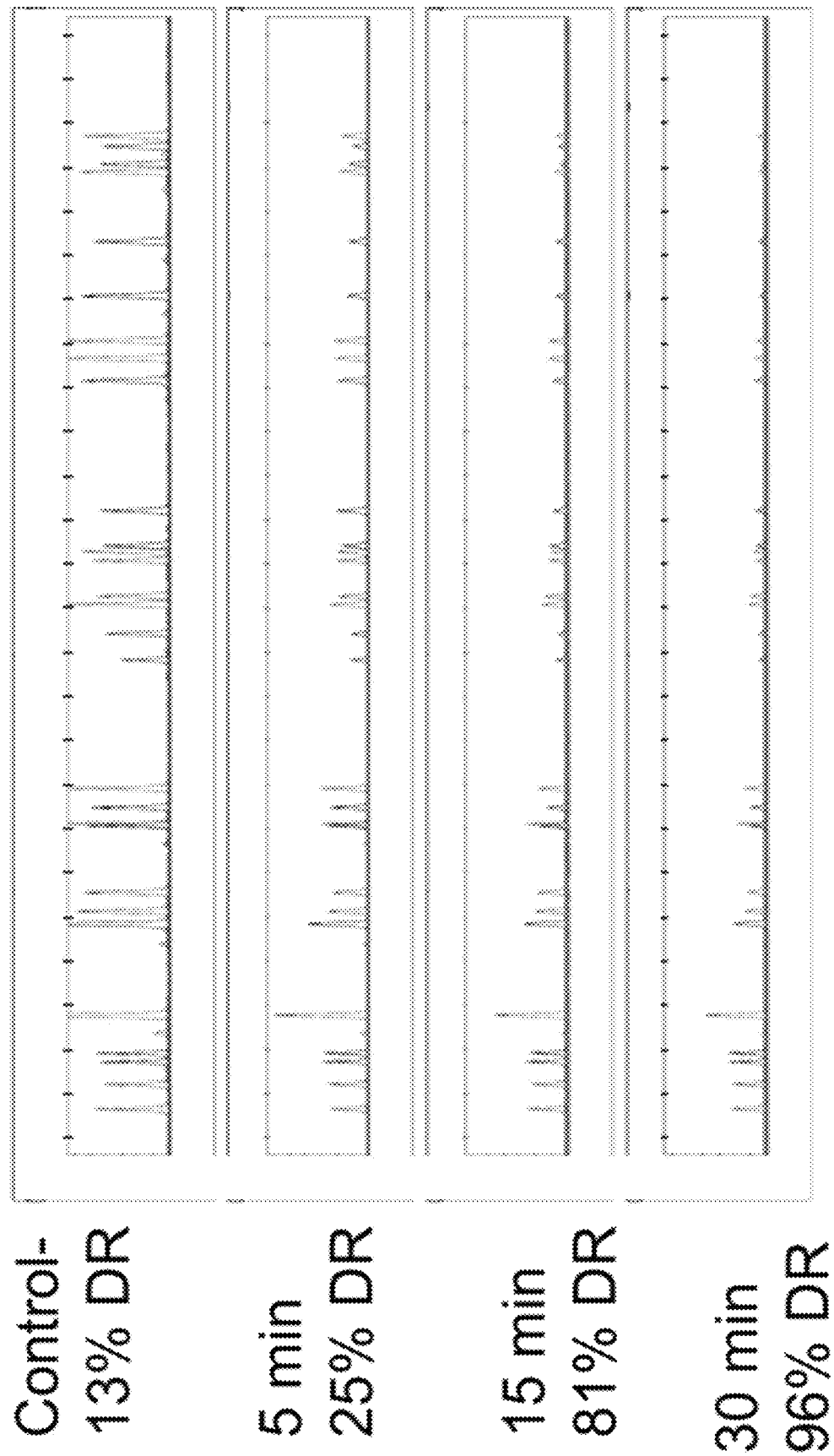
FIG. 12 shows STR results for 1 ng targeted DNase I treated samples.
Figure 13:
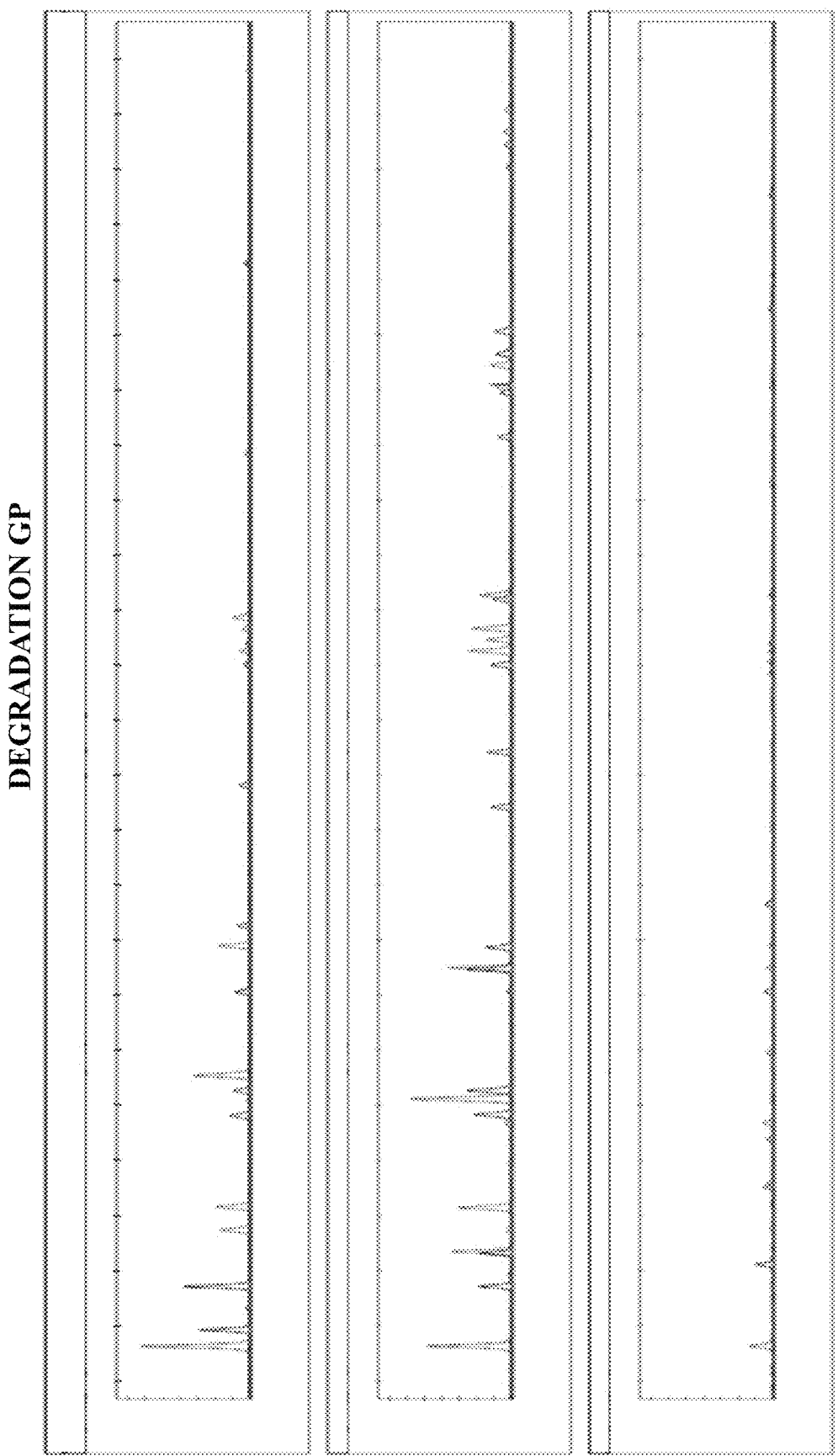
FIG. 13 shows STR results for 200 pg targeted environmentally degraded samples.

Downstream STR analysis of the degraded samples was performed using the Identifiler® Plus STR kit (Applied Biosystems/Life Technologies), targeting 3 different DNA concentrations: 1 ng (manufacturer recommended target amount), 500 pg, and 200 pg. In all instances, the STR results mirrored the degradation ratios calculated by this duel target quantification assay, the preferred embodiment of the present invention. As the degradation increased, the typical "ski slope" effect was observed in the STR results, until eventually, no results (or very partial, inconclusive results) were observed at the highest extent of the degradation. The extent of the degradation was observed to a much higher level at the low concentrations of DNA (500 pg and 200 pg). As expected, lower RFUs and in some instances, no results, were observed when the DNA was both degraded and low in amount. FIGS. 11 through 13 show the STR results of the degradation study.

Example 12: Species Specificity

A quantification system used for forensic DNA samples must not react to non-primate DNA, as the STR systems commonly used in crime laboratories are only reactive to human and primate DNA. Three primates, seven non-primate mammals, and five prokaryotic species were analyzed using theInnoQuant Quantification Kit™, the analyses including Yb8, SVA and the 172 bp IPC target. DNA purified from two species of dogs, two cats, deer, rat, mouse, mosquito, chicken, green monkey, chimpanzee, orangutan, *Escherichia coli*, *Ralstonia eutropha*, *Rhodococcus* rubber, yeast, and *Staphylococcus aureus* were run in duplicate. The DNA samples were at 5 ng/µl. A sample was considered "reactive" if >1 pg/µl of DNA was detected with the process of the present invention using a human DNA standard curve.

Figure 14:
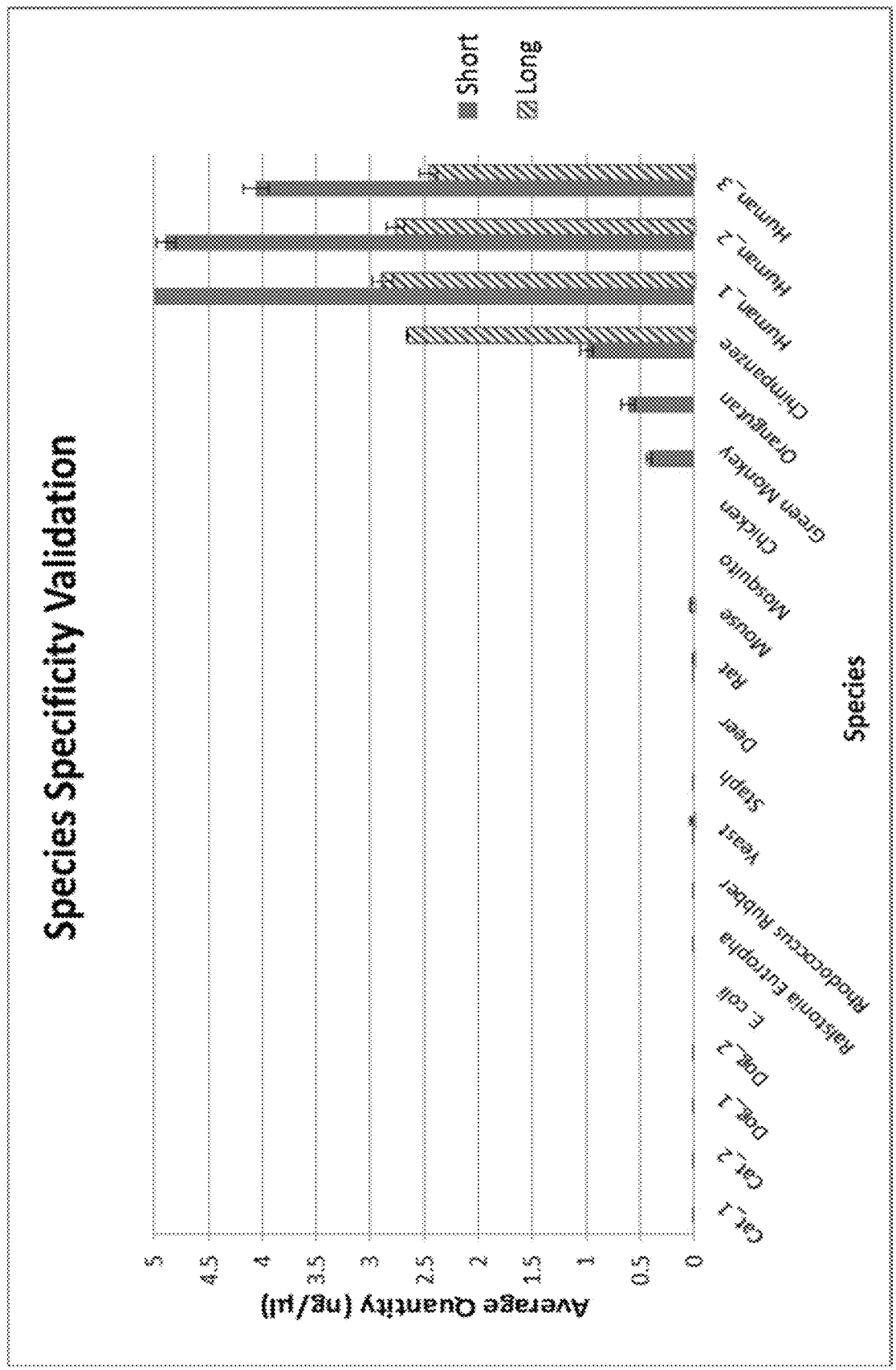
FIG. 14 shows species study results (striped red bars show long target SVA; solid blue bars show short target Yb8).

Of the species tested, only higher primate samples were reactive (FIG. 14). Cross reactivity of non-human primate species with the commonly used STR systems has been previously demonstrated. These results demonstrate that the process of the present invention is adequately species-specific for forensic use and does not yield quantitative results with non-primate samples.

Example 13: Four Target System (Yb8, SVA, Y Deletion, and IPC)

The addition of a male specific target to the real-time PCR quantitation multiplex is useful to detect the amount of male DNA in samples that contain large quantities of female DNA and low quantities of male DNA. A region of the human Y chromosome DNA containing a 90 base pair sequence which is deleted on the human X-chromosome in an X-Y chromosome homologous region was selected by using a primer pair specific to the human Y chromosome DNA in order to obtain amplified products (Walker, et al., Anal. Biochem. 337(1): 89-97 (2005)).

Example 14: Multiplex Reaction

Figure 16A:
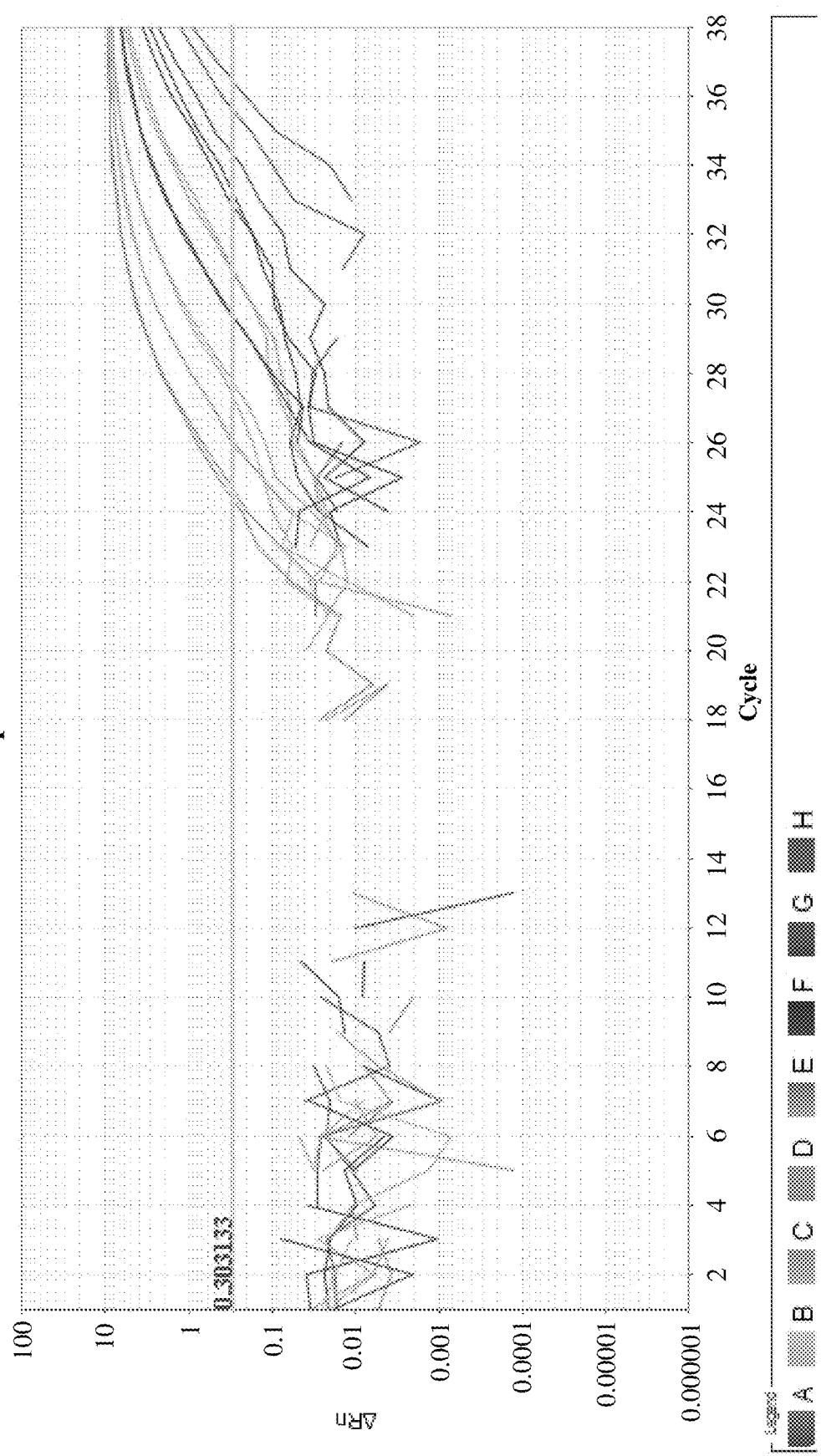
FIG. 16A shows the amplification plot of the Y chromosome target in a four-target multiplex reaction.
Figure 16B:
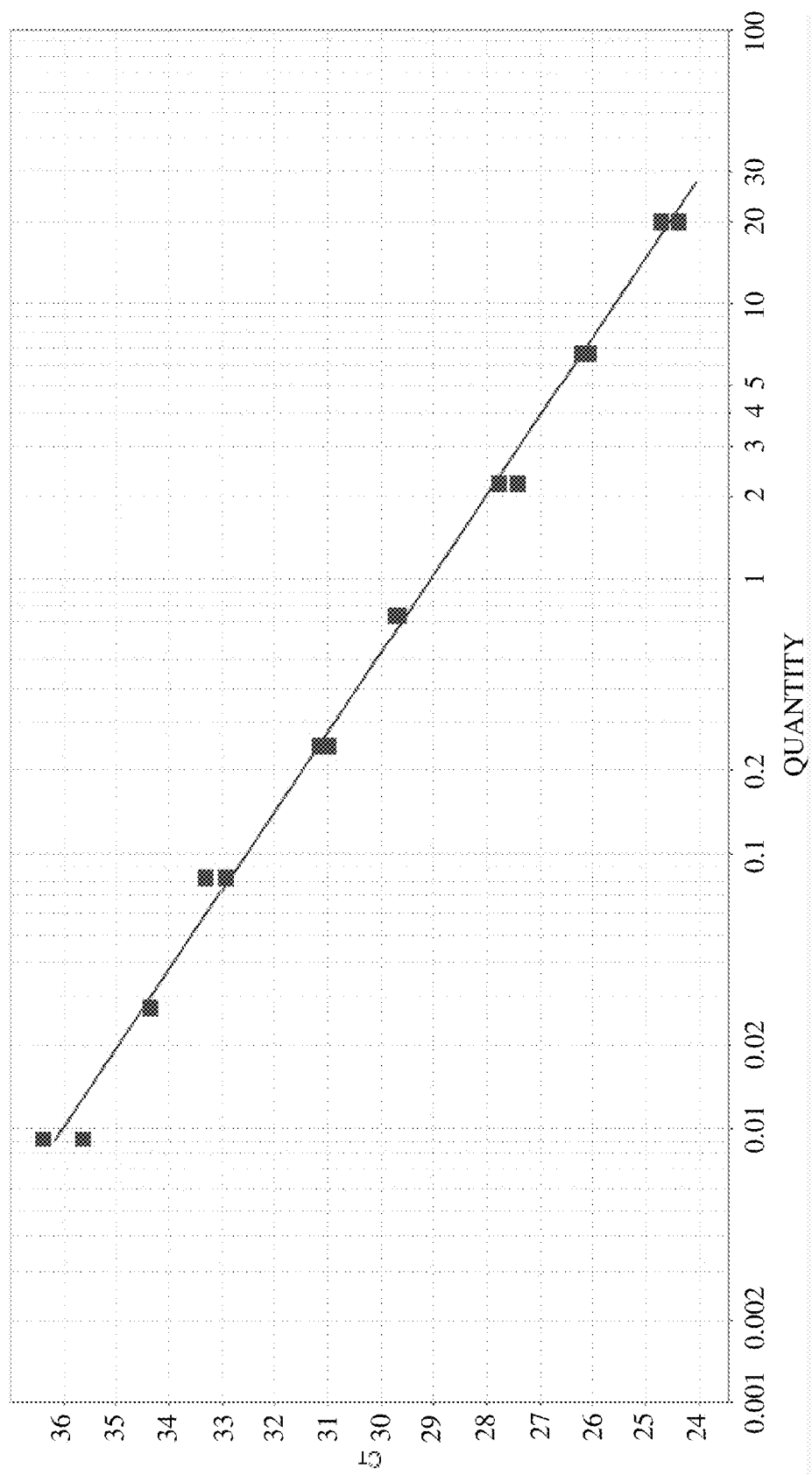
FIG. 16B shows the standard curve of the Y chromosome target in a four-target multiplex reaction.

When added to the multiplex, the male specific fragment is labeled in FAM, the "short" Yb8 fragment in JOE, the "long" SVA fragment in Cy5 and the 158 bp internal positive control (IPC) to assess the presence or absence of inhibitors in the sample in Cy3. The cycle number of the multiplex was increased from 32 to 35 and 38. Thirty-eight cycles produced adequate results, with efficiencies of the three targets, SVA, Yb8, and Y, at 88%, 99%, and 94%, respectively. See FIGS. 16A and 16B for the amplification plot and standard curve, respectively, of the Y chromosome target in a four-target multiplex reaction.

While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made. It should be appreciated that the scope of this invention is not limited to the detailed description of the invention hereinabove, which is intended merely to be illustrative, but rather comprehends the subject matter defined by the following claims.

What is claimed is:

1. A process for determining the concentration of a first retrotransposon interspersed element and the concentration of a second retrotransposon interspersed element within a sample, the process comprising the steps of:

providing a sample comprising human DNA, wherein the sample comprises a first retrotransposon interspersed element and a second retrotransposon interspersed element, the first retrotransposon interspersed element is an Alu element found in human genome, and the second retrotransposon interspersed element is an SVA element of human retinitis pigmentosa (RP) gene, providing a first probe comprising a first moiety capable of producing a first fluorescent signal at a first wavelength and a first quencher wherein the first quencher quenches the first fluorescent signal produced by the first moiety before the first probe hybridizes to its target nucleic acid and the first probe is complementary to the first retrotransposon interspersed element, providing a second probe comprising a second moiety capable of producing a second fluorescent signal at a second wavelength and a second quencher wherein the second quencher quenches the second fluorescent signal produced by the second moiety before the second probe hybridizes to its target nucleic acid, the second probe is complementary to the second retrotransposon interspersed element, and the first moiety is different from the second moiety, providing at least one primer specific for the first retrotransposon interspersed element and the at least one primer specific for the second retrotransposon interspersed element, providing a Taq polymerase, performing a real time polymerase chain reaction (PCR) by amplifying the first retrotransposon interspersed element and the second retrotransposon interspersed element from the sample in the presence of the first probe, the second probe, the at least one primer specific for the first retrotransposon interspersed element, the at least one primer specific for the second retrotransposon interspersed element, and the Taq polymerase such that, during the process of the real time PCR, the Taq polymerase cleaves the first probe and separates the first moiety from the first quencher on the first probe, cleaves the second probe to separate the second fluorescent moiety from the second quencher on the second probe, and the first fluorescent signal and the second fluorescent signal are produced, wherein the real time PCR is performed for a plurality of polymerase chain reaction cycles, measuring the the first fluorescent signal and the second fluorescent signal in each of the polymerase chain reaction cycles, determining a first cycle threshold of the real time PCR based on the first fluorescent signal in each of the polymerase chain reaction cycles and a second cycle threshold of the real time PCR based on the second fluorescent signal in each of the polymerase chain reaction cycles, and determining the concentration of the first retrotransposon interspersed element and the concentration of the second retrotransposon interspersed element within the sample by comparing the first cycle threshold and the second cycle threshold with cycle thresholds in standard curves produced using different concentrations of the first retrotransposon interspersed element and the second retrotransposon interspersed element.

2. The process of claim 1, the first retrotransposon interspersed element consisting of 40 to 150 base pairs and the second retrotransposon interspersed element consisting of 120 to 400 base pairs.

3. The process of claim 1, the first retrotransposon interspersed element being a target sequence that has about 80 base pairs and is an Alu element of subfamily Yb8 and the second retrotransposon interspersed element being a target sequence that has about 200-400 base pairs.

4. The process of claim 3, wherein the at least one primer specific for the first retrotransposon interspersed element and the at least one primer specific for the second retrotransposon interspersed element are selected from the group consisting of SEQ ID NOS: 5, 6, 8, 9, and 11-15:

```
                                                (SEQ ID NO: 5)
5' GGAAGCGGAGCTTGCAGTGA 3'

(SEQ ID NO: 6)
5' AGACGGAGTCTCGCTCTGTCGC 3'

(SEQ ID NO: 8)
5' TGGGATCCTGTTGATCTGTGACCT 3'

(SEQ ID NO: 9)
5' GATTTGGCAGGGTCATGGGACAAT 3'

(SEQ ID NO: 11)
5' ATGTGCTGTGTCCACTCAGGGTTA 3'

(SEQ ID NO: 12)
5' TTCTTGGGTGTTTCTCACAGAGGG 3'

(SEQ ID NO: 13)
5' ATTCTTGGGTGTTTCTCACAGAGG 3'

(SEQ ID NO: 14)
5' CCAACCCTGTGCTCTCTGAAAC 3'

(SEQ ID NO: 15)
5' TTTGGCAGGGTCATGGGACAA 3'.
```

5. The process of claim 4, wherein the Alu element of subfamily Yb8 and the SVA element of human RP gene are amplified simultaneously in a single reaction mixture.

6. The process of claim 1 where the Alu element of subfamily Yb8 is an Alu Yb8 element.

7. The process of claim 3, wherein the at least one probe of the first probe and the second probe is selected from the group consisting of SEQ ID NO: 7 and SEQ ID NO: 10:

```
                                                (SEQ ID NO: 7)
5' AGATTGCGCCACTGCAGTCCGCAG 3'

(SEQ ID NO: 10)
5' AAGGGCGGTGCAAGATGTGCTTTGTT 3'.
```

8. The process of claim 3, wherein the at least one probe of the first probe and the second probe is selected from the group consisting of SEQ ID NOS: 4, 7 and 10:

```
                                                (SEQ ID NO: 4)
5'-ATCACGAGGTCAGGAGATCGAGACCAT-3'

(SEQ ID NO: 7)
5'-AGATTGCGCCACTGCAGTCCGCAG-3 '

(SEQ ID NO: 10)
5'-AACJGGCGGTGCAAGATGTGCTTIGTT-3'.
```

9. The process of claim 1, the process further comprising detecting the amount of human male DNA in the sample based on amplifying a human male specific DNA sequence in the presence of at least one primer, a third probe and Taq polymerase wherein the sample contains large quantities of human female DNA and low quantities of the human male DNA, and the human male specific DNA sequence is a 90 bp Y-chromosome specific DNA sequence which is deleted on human X-chromosomes.

10. The process of claim 9, the process further comprising assessing an extent of human male DNA and human female DNA in the sample.

11. The process of claim 9, wherein the at least one primer for amplifying the human male specific DNA sequence is selected from the group consisting of SEQ ID NO: 25 and SEQ ID NO: 26:

```
                                                (SEQ ID NO: 25)
5' CAATGTGCTAGGCTCTAGGAATAC 3'

(SEQ ID NO: 26)
5' AAGAGTGTCATGGCTCAAAGAG 3'.
```

12. The process of claim 9, the third probe consists of SEQ ID NO: 27:

```
                                                (SEQ ID NO: 27)
5' AGAGAGTATGACAAACATGGCATGGGC 3'.
```

13. The process of claim 9, the process further comprising:
forming a sample mixture by adding an internal positive control to the sample and amplifying the internal positive control in the sample mixture.

14. The process of claim 13, wherein the internal positive control comprises a synthetic nucleotide sequence.

15. The process of claim 1, further comprising assessing an extent of degradation of the human DNA in the sample based on relative amounts of the first retrotransposon interspersed element and the second retrotransposon interspersed element.

* * * * *